(12) United States Patent
Kurukchi et al.

(10) Patent No.: US 8,829,256 B2
(45) Date of Patent: *Sep. 9, 2014

(54) PROCESSES AND SYSTEMS FOR FRACTIONATION OF BROMINATED HYDROCARBONS IN THE CONVERSION OF NATURAL GAS TO LIQUID HYDROCARBONS

(75) Inventors: Sabah A. Kurukchi, Houston, TX (US); Yijun Liu, Houston, TX (US)

(73) Assignee: GTC Technology US, LLC, Houston, TX (US)

( * ) Notice: Subject to any disclaimer, the term of this patent is extended or adjusted under 35 U.S.C. 154(b) by 362 days.

This patent is subject to a terminal disclaimer.

(21) Appl. No.: 13/173,847

(22) Filed: Jun. 30, 2011

(65) Prior Publication Data

US 2013/0006024 A1    Jan. 3, 2013

(51) Int. Cl.
| | |
|---|---|
| *C07C 17/00* | (2006.01) |
| *C07C 17/383* | (2006.01) |
| *C07C 17/23* | (2006.01) |
| *C01B 7/09* | (2006.01) |
| *C07C 17/10* | (2006.01) |
| *C01B 7/00* | (2006.01) |

(52) U.S. Cl.
CPC ............. *C07C 17/10* (2013.01); *C07C 17/383* (2013.01); *C07C 17/23* (2013.01); *C01B 7/093* (2013.01); *C01B 7/00* (2013.01); *B01J 2219/00006* (2013.01)
USPC ........................................................ 570/255

(58) Field of Classification Search
None
See application file for complete search history.

(56) References Cited

U.S. PATENT DOCUMENTS

| | | |
|---|---|---|
| 2,168,260 A | 8/1939 | Heisel et al. |
| 2,246,082 A | 6/1941 | Vaughan et al. |
| 2,320,257 A | 5/1943 | Beekhuis |
| 2,488,083 A | 11/1949 | Gorin et al. |
| 2,536,457 A | 1/1951 | Mugdan |
| 2,666,024 A | 1/1954 | Low et al. |
| 2,677,598 A | 5/1954 | Crummett et al. |
| 2,809,930 A | 10/1957 | Miller |
| 2,941,014 A | 6/1960 | Rothweiler et al. |
| 3,076,784 A | 2/1963 | Schulte-Huemann et al. |
| 3,172,915 A | 3/1965 | Borkowski et al. |
| 3,181,934 A | 5/1965 | Davis |
| 3,233,972 A | 2/1966 | Walker et al. |
| 3,240,564 A | 3/1966 | Uffelmann et al. |
| 3,246,043 A | 4/1966 | Rosset et al. |
| 3,254,023 A | 5/1966 | Miale et al. |
| 3,273,964 A | 9/1966 | Rosset |
| 3,291,708 A | 12/1966 | Juda |
| 3,294,846 A | 12/1966 | Livak et al. |
| 3,310,380 A | 3/1967 | Lester |
| 3,314,762 A | 4/1967 | Hahn |
| 3,346,340 A | 10/1967 | Louvar et al. |
| 3,353,916 A | 11/1967 | Lester |
| 3,353,919 A | 11/1967 | Stockman |
| 3,379,506 A | 4/1968 | Massonne et al. |
| 3,468,968 A | 9/1969 | Baker et al. |
| 3,496,242 A | 2/1970 | Berkowitz et al. |
| 3,562,321 A | 2/1971 | Borkowski et al. |
| 3,598,876 A | 8/1971 | Bloch |
| 3,615,265 A | 10/1971 | Gartner |
| 3,642,447 A | 2/1972 | Hahn et al. |
| 3,657,367 A | 4/1972 | Blake et al. |
| 3,670,037 A | 6/1972 | Dugan |
| 3,673,264 A | 6/1972 | Kuhn |
| 3,679,758 A | 7/1972 | Schneider |
| 3,702,886 A | 11/1972 | Argauer et al. |
| 3,705,196 A | 12/1972 | Turner |
| 3,799,997 A | 3/1974 | Schmerling |
| 3,816,599 A | 6/1974 | Kafes |
| 3,865,886 A | 2/1975 | Schindler et al. |
| 3,876,715 A | 4/1975 | McNulty et al. |
| 3,879,473 A | 4/1975 | Stapp |
| 3,879,480 A | 4/1975 | Riegel et al. |
| 3,883,651 A | 5/1975 | Woitun et al. |
| 3,886,287 A | 5/1975 | Kobayashi et al. |
| 3,894,103 A | 7/1975 | Chang et al. |
| 3,894,104 A | 7/1975 | Chang et al. |
| 3,894,105 A | 7/1975 | Chang et al. |
| 3,894,107 A | 7/1975 | Butter et al. |
| 3,907,917 A | 9/1975 | Forth |
| 3,919,336 A | 11/1975 | Kurtz |
| 3,920,764 A | 11/1975 | Riegel et al. |
| 3,923,913 A | 12/1975 | Antonini et al. |
| 3,927,111 A | 12/1975 | Robinson |
| 3,928,483 A | 12/1975 | Chang et al. |

(Continued)

FOREIGN PATENT DOCUMENTS

| | | |
|---|---|---|
| CA | 1099656 | 4/1981 |
| CA | 1101441 | 5/1981 |

(Continued)

OTHER PUBLICATIONS

Abstract of BE 812868, Aromatic hydrocarbons prodn. from chlorinated hydrocarbons, Publication date: Sep. 27, 1974, esp@cenet database—worldwide.
Abstract of BE 814900, Volatile aramatic cpds. prodn., Publication date: Sep. 2, 1974, esp@cenet database—worldwide.
Abstract of BR 0210054, Oxidative halogenation of C1 hydrocarbons to halogenated C1 hydrocarbons and integrated processes related thereto, Publication date: Aug. 17, 2004, Inventor: Schweizer et al., esp@cenet database—worldwide.
Abstract of CA 2447761 A1, Oxidative halogenation of C1 hydrocarbons to halogenated C1 hydrocarbons and integrated processes related thereto, Publication date: Nov. 28, 2002, Inventor: Hickman, et al.
Abstract of CA 2471295 A1, Integrated process for synthesizing alcohols, ethers, and olefins from alkanes, Publication date: Jul. 31, 2003, Inventor: Sherman et al.

(Continued)

*Primary Examiner* — Sudhakar Katakam
(74) *Attorney, Agent, or Firm* — Tumey L.L.P.

(57) ABSTRACT

Process and systems for converting lower molecular weight alkanes to higher molecular weight hydrocarbons that include fractionation of brominated hydrocarbons, wherein the brominated hydrocarbons are formed by reaction of the lower molecular weight alkanes with bromine.

30 Claims, 5 Drawing Sheets

(56) References Cited

U.S. PATENT DOCUMENTS

| | | |
|---|---|---|
| 3,959,450 A | 5/1976 | Calloue et al. |
| 3,965,205 A | 6/1976 | Garwood et al. |
| 3,974,062 A | 8/1976 | Owen et al. |
| 3,987,119 A | 10/1976 | Kurtz et al. |
| 3,992,466 A | 11/1976 | Plank et al. |
| 4,006,169 A | 2/1977 | Anderson et al. |
| 4,011,278 A | 3/1977 | Plank et al. |
| 4,025,571 A | 5/1977 | Lago |
| 4,025,572 A | 5/1977 | Lago |
| 4,025,575 A | 5/1977 | Chang et al. |
| 4,025,576 A | 5/1977 | Chang et al. |
| 4,035,285 A | 7/1977 | Owen et al. |
| 4,035,430 A | 7/1977 | Dwyer et al. |
| 4,039,600 A | 8/1977 | Chang |
| 4,044,061 A | 8/1977 | Chang et al. |
| 4,046,819 A | 9/1977 | Schmerling |
| 4,046,825 A | 9/1977 | Owen et al. |
| 4,049,734 A | 9/1977 | Garwood et al. |
| 4,052,471 A | 10/1977 | Pearsall |
| 4,052,472 A | 10/1977 | Givens et al. |
| 4,058,576 A | 11/1977 | Chang et al. |
| 4,060,568 A | 11/1977 | Rodewald |
| 4,071,753 A | 1/1978 | Fulenwider et al. |
| 4,072,733 A | 2/1978 | Hargis et al. |
| 4,087,475 A | 5/1978 | Jordan |
| 4,088,706 A | 5/1978 | Kaeding |
| 4,092,368 A | 5/1978 | Smith |
| 4,105,755 A | 8/1978 | Darnell et al. |
| 4,110,180 A | 8/1978 | Nidola et al. |
| 4,117,251 A | 9/1978 | Kaufhold et al. |
| 4,129,604 A | 12/1978 | Tsao |
| 4,133,838 A | 1/1979 | Pearson |
| 4,133,966 A | 1/1979 | Pretzer et al. |
| 4,138,440 A | 2/1979 | Chang et al. |
| 4,143,084 A | 3/1979 | Kaeding et al. |
| 4,156,698 A | 5/1979 | Dwyer et al. |
| 4,169,862 A | 10/1979 | Eden |
| 4,172,099 A | 10/1979 | Severino |
| 4,187,255 A | 2/1980 | Dodd |
| 4,191,618 A | 3/1980 | Coker et al. |
| 4,194,990 A | 3/1980 | Pieters et al. |
| 4,197,420 A | 4/1980 | Ferraris et al. |
| 4,219,604 A | 8/1980 | Kakimi et al. |
| 4,219,680 A | 8/1980 | Konig et al. |
| 4,249,031 A | 2/1981 | Drent et al. |
| 4,252,687 A | 2/1981 | Dale et al. |
| 4,270,929 A | 6/1981 | Dang Vu et al. |
| 4,272,338 A | 6/1981 | Lynch et al. |
| 4,282,159 A | 8/1981 | Davidson et al. |
| 4,300,005 A | 11/1981 | Li |
| 4,300,009 A | 11/1981 | Haag et al. |
| 4,301,253 A | 11/1981 | Warren |
| 4,302,619 A | 11/1981 | Gross et al. |
| 4,307,261 A | 12/1981 | Beard, Jr. et al. |
| 4,308,403 A | 12/1981 | Knifton |
| 4,311,865 A | 1/1982 | Chen et al. |
| 4,317,800 A | 3/1982 | Sloterdijk et al. |
| 4,317,934 A | 3/1982 | Seemuth |
| 4,317,943 A | 3/1982 | Knifton |
| 4,320,241 A | 3/1982 | Frankiewicz |
| 4,333,852 A | 6/1982 | Warren |
| 4,347,391 A | 8/1982 | Campbell |
| 4,350,511 A | 9/1982 | Holmes et al. |
| 4,356,159 A | 10/1982 | Norval et al. |
| 4,371,716 A | 2/1983 | Paxson et al. |
| 4,373,109 A | 2/1983 | Olah |
| 4,376,019 A | 3/1983 | Gamlen et al. |
| 4,379,734 A | 4/1983 | Franzen |
| 4,380,682 A | 4/1983 | Leitert et al. |
| 4,384,159 A | 5/1983 | Diesen |
| 4,389,391 A | 6/1983 | Dunn, Jr. |
| 4,410,714 A | 10/1983 | Apanel |
| 4,412,086 A | 10/1983 | Beard, Jr. et al. |
| 4,418,236 A | 11/1983 | Cornelius et al. |
| 4,431,856 A | 2/1984 | Daviduk et al. |
| 4,433,189 A | 2/1984 | Young |
| 4,433,192 A | 2/1984 | Olah |
| 4,439,409 A | 3/1984 | Puppe et al. |
| 4,440,871 A | 4/1984 | Lok et al. |
| 4,443,620 A | 4/1984 | Gelbein et al. |
| 4,462,814 A | 7/1984 | Holmes et al. |
| 4,465,884 A | 8/1984 | Degnan et al. |
| 4,465,893 A | 8/1984 | Olah |
| 4,467,130 A | 8/1984 | Olah |
| 4,467,133 A | 8/1984 | Chang et al. |
| 4,489,210 A | 12/1984 | Judat et al. |
| 4,489,211 A | 12/1984 | Ogura et al. |
| 4,492,657 A | 1/1985 | Heiss |
| 4,496,752 A | 1/1985 | Gelbein et al. |
| 4,497,967 A | 2/1985 | Wan |
| 4,499,314 A | 2/1985 | Seddon et al. |
| 4,506,105 A | 3/1985 | Kaufhold |
| 4,509,955 A | 4/1985 | Hayashi |
| 4,513,092 A | 4/1985 | Chu et al. |
| 4,513,164 A | 4/1985 | Olah |
| 4,523,040 A | 6/1985 | Olah |
| 4,524,227 A | 6/1985 | Fowles et al. |
| 4,524,228 A | 6/1985 | Fowles et al. |
| 4,524,231 A | 6/1985 | Fowles et al. |
| 4,538,014 A | 8/1985 | Miale et al. |
| 4,538,015 A | 8/1985 | Miale et al. |
| 4,540,826 A | 9/1985 | Banasiak et al. |
| 4,543,434 A | 9/1985 | Chang |
| 4,544,781 A | 10/1985 | Chao et al. |
| 4,547,612 A | 10/1985 | Tabak |
| 4,550,217 A | 10/1985 | Graziani et al. |
| 4,550,218 A | 10/1985 | Chu |
| 4,568,660 A | 2/1986 | Klosiewicz |
| 4,579,977 A | 4/1986 | Drake |
| 4,579,992 A | 4/1986 | Kaufhold et al. |
| 4,579,996 A | 4/1986 | Font Freide et al. |
| 4,587,375 A | 5/1986 | Debras et al. |
| 4,588,835 A | 5/1986 | Torii et al. |
| 4,590,310 A | 5/1986 | Townsend et al. |
| 4,599,474 A | 7/1986 | Devries et al. |
| 4,605,796 A | 8/1986 | Isogai et al. |
| 4,605,803 A | 8/1986 | Chang et al. |
| 4,621,161 A | 11/1986 | Shihabi |
| 4,621,164 A | 11/1986 | Chang et al. |
| 4,626,607 A | 12/1986 | Jacquinot et al. |
| 4,633,027 A | 12/1986 | Owen et al. |
| 4,634,800 A | 1/1987 | Withers, Jr. et al. |
| 4,642,403 A | 2/1987 | Hyde et al. |
| 4,642,404 A | 2/1987 | Shihabi |
| 4,652,688 A | 3/1987 | Brophy et al. |
| 4,654,449 A | 3/1987 | Chang et al. |
| 4,655,893 A | 4/1987 | Beale |
| 4,658,073 A | 4/1987 | Tabak |
| 4,658,077 A | 4/1987 | Kolts et al. |
| 4,665,259 A | 5/1987 | Brazdil et al. |
| 4,665,267 A | 5/1987 | Barri |
| 4,665,270 A | 5/1987 | Brophy et al. |
| 4,675,410 A | 6/1987 | Feitler et al. |
| 4,690,903 A | 9/1987 | Chen et al. |
| 4,695,663 A | 9/1987 | Hall et al. |
| 4,696,985 A | 9/1987 | Martin |
| 4,704,488 A | 11/1987 | Devries et al. |
| 4,704,493 A | 11/1987 | Devries et al. |
| 4,709,108 A | 11/1987 | Devries et al. |
| 4,720,600 A | 1/1988 | Beech, Jr. et al. |
| 4,720,602 A | 1/1988 | Chu |
| 4,724,275 A | 2/1988 | Hinnenkamp et al. |
| 4,725,425 A | 2/1988 | Lesher et al. |
| 4,735,747 A | 4/1988 | Ollivier et al. |
| 4,737,594 A | 4/1988 | Olah |
| 4,748,013 A | 5/1988 | Saito et al. |
| 4,762,596 A | 8/1988 | Huang et al. |
| 4,769,504 A | 9/1988 | Noceti et al. |
| 4,774,216 A | 9/1988 | Kolts et al. |
| 4,775,462 A | 10/1988 | Imai et al. |
| 4,777,321 A | 10/1988 | Harandi et al. |
| 4,781,733 A | 11/1988 | Babcock et al. |
| 4,783,566 A | 11/1988 | Kocal et al. |
| 4,788,369 A | 11/1988 | Marsh et al. |

(56) References Cited

U.S. PATENT DOCUMENTS

| | | |
|---|---|---|
| 4,788,377 A | 11/1988 | Chang et al. |
| 4,792,642 A | 12/1988 | Rule et al. |
| 4,795,732 A | 1/1989 | Barri |
| 4,795,737 A | 1/1989 | Rule et al. |
| 4,795,843 A | 1/1989 | Imai et al. |
| 4,795,848 A | 1/1989 | Teller et al. |
| 4,804,797 A | 2/1989 | Minet et al. |
| 4,804,800 A | 2/1989 | Bortinger et al. |
| 4,808,763 A | 2/1989 | Shum |
| 4,814,527 A | 3/1989 | Diesen |
| 4,814,532 A | 3/1989 | Yoshida et al. |
| 4,814,535 A | 3/1989 | Yurchak |
| 4,814,536 A | 3/1989 | Yurchak |
| 4,849,562 A | 7/1989 | Buhs et al. |
| 4,849,573 A | 7/1989 | Kaefing |
| 4,851,602 A | 7/1989 | Harandi et al. |
| 4,851,606 A | 7/1989 | Ragonese et al. |
| 4,886,925 A | 12/1989 | Harandi |
| 4,886,932 A | 12/1989 | Leyshon |
| 4,891,463 A | 1/1990 | Chu |
| 4,895,995 A | 1/1990 | James, Jr. et al. |
| 4,899,000 A | 2/1990 | Stauffer |
| 4,899,001 A | 2/1990 | Kalnes et al. |
| 4,899,002 A | 2/1990 | Harandi et al. |
| 4,902,842 A | 2/1990 | Kalnes et al. |
| 4,925,995 A | 5/1990 | Robschlager |
| 4,929,781 A | 5/1990 | James, Jr. et al. |
| 4,939,310 A | 7/1990 | Wade |
| 4,939,311 A | 7/1990 | Washecheck et al. |
| 4,939,314 A | 7/1990 | Harandi et al. |
| 4,945,175 A | 7/1990 | Hobbs et al. |
| 4,950,811 A | 8/1990 | Doussain et al. |
| 4,950,822 A | 8/1990 | Dileo et al. |
| 4,956,521 A | 9/1990 | Volles |
| 4,962,252 A | 10/1990 | Wade |
| 4,973,776 A | 11/1990 | Allenger et al. |
| 4,973,786 A | 11/1990 | Karra |
| 4,982,024 A | 1/1991 | Lin et al. |
| 4,982,041 A | 1/1991 | Campbell |
| 4,988,660 A | 1/1991 | Campbell |
| 4,990,696 A | 2/1991 | Stauffer |
| 4,990,711 A | 2/1991 | Chen et al. |
| 5,001,293 A | 3/1991 | Nubel et al. |
| 5,004,847 A | 4/1991 | Beaver et al. |
| 5,013,424 A | 5/1991 | James, Jr. et al. |
| 5,013,793 A | 5/1991 | Wang et al. |
| 5,019,652 A | 5/1991 | Taylor et al. |
| 5,026,934 A | 6/1991 | Bains et al. |
| 5,026,937 A | 6/1991 | Bricker |
| 5,026,944 A | 6/1991 | Allenger et al. |
| 5,034,566 A | 7/1991 | Ishino et al. |
| 5,043,502 A | 8/1991 | Martindale et al. |
| 5,055,235 A | 10/1991 | Brackenridge et al. |
| 5,055,625 A | 10/1991 | Neidiffer et al. |
| 5,055,633 A | 10/1991 | Volles |
| 5,055,634 A | 10/1991 | Volles |
| 5,059,744 A | 10/1991 | Harandi et al. |
| 5,068,478 A | 11/1991 | Miller et al. |
| 5,071,449 A | 12/1991 | Sircar |
| 5,071,815 A | 12/1991 | Wallace et al. |
| 5,073,656 A | 12/1991 | Chafin et al. |
| 5,073,657 A | 12/1991 | Warren |
| 5,082,473 A | 1/1992 | Keefer |
| 5,082,816 A | 1/1992 | Teller et al. |
| 5,085,674 A | 2/1992 | Leavitt |
| 5,087,779 A | 2/1992 | Nubel et al. |
| 5,087,786 A | 2/1992 | Nubel et al. |
| 5,087,787 A | 2/1992 | Kimble et al. |
| 5,093,533 A | 3/1992 | Wilson |
| 5,093,542 A | 3/1992 | Gaffney |
| 5,096,469 A | 3/1992 | Keefer |
| 5,097,083 A | 3/1992 | Stauffer |
| 5,099,084 A | 3/1992 | Stauffer |
| 5,105,045 A | 4/1992 | Kimble et al. |
| 5,105,046 A | 4/1992 | Washecheck |
| 5,107,032 A | 4/1992 | Erb et al. |
| 5,107,051 A | 4/1992 | Pannell |
| 5,107,061 A | 4/1992 | Ou et al. |
| 5,108,579 A | 4/1992 | Casci |
| 5,118,899 A | 6/1992 | Kimble et al. |
| 5,120,332 A | 6/1992 | Wells |
| 5,132,343 A | 7/1992 | Zwecker et al. |
| 5,138,112 A | 8/1992 | Gosling et al. |
| 5,139,991 A | 8/1992 | Taylor et al. |
| 5,146,027 A | 9/1992 | Gaffney |
| 5,157,189 A | 10/1992 | Karra |
| 5,160,502 A | 11/1992 | Kimble et al. |
| 5,166,452 A | 11/1992 | Gradl et al. |
| 5,175,382 A | 12/1992 | Hebgen et al. |
| 5,178,748 A | 1/1993 | Casci et al. |
| 5,185,479 A | 2/1993 | Stauffer |
| 5,188,725 A | 2/1993 | Harandi |
| 5,191,142 A | 3/1993 | Marshall et al. |
| 5,194,244 A | 3/1993 | Brownscombe et al. |
| 5,202,506 A | 4/1993 | Kirchner et al. |
| 5,202,511 A | 4/1993 | Salinas, III et al. |
| 5,208,402 A | 5/1993 | Wilson |
| 5,210,357 A | 5/1993 | Kolts et al. |
| 5,215,648 A | 6/1993 | Zones et al. |
| 5,223,471 A | 6/1993 | Washecheck |
| 5,228,888 A | 7/1993 | Gmelin et al. |
| 5,233,113 A | 8/1993 | Periana et al. |
| 5,237,115 A | 8/1993 | Makovec et al. |
| 5,243,098 A | 9/1993 | Miller et al. |
| 5,243,114 A | 9/1993 | Johnson et al. |
| 5,245,109 A | 9/1993 | Kaminsky et al. |
| 5,254,772 A | 10/1993 | Dukat et al. |
| 5,254,790 A | 10/1993 | Thomas et al. |
| 5,264,635 A | 11/1993 | Le et al. |
| 5,268,518 A | 12/1993 | West et al. |
| 5,276,226 A | 1/1994 | Horvath et al. |
| 5,276,240 A | 1/1994 | Timmons et al. |
| 5,276,242 A | 1/1994 | Wu |
| 5,284,990 A | 2/1994 | Peterson et al. |
| 5,300,126 A | 4/1994 | Brown et al. |
| 5,306,855 A | 4/1994 | Periana et al. |
| 5,316,995 A | 5/1994 | Kaminsky et al. |
| 5,319,132 A | 6/1994 | Ozawa et al. |
| 5,334,777 A | 8/1994 | Miller et al. |
| 5,345,021 A | 9/1994 | Casci et al. |
| 5,354,916 A | 10/1994 | Horvath et al. |
| 5,354,931 A | 10/1994 | Jan et al. |
| 5,358,645 A | 10/1994 | Hong et al. |
| 5,366,949 A | 11/1994 | Schubert |
| 5,371,313 A | 12/1994 | Ostrowicki |
| 5,382,704 A | 1/1995 | Krespan et al. |
| 5,382,743 A | 1/1995 | Beech, Jr. et al. |
| 5,382,744 A | 1/1995 | Abbott et al. |
| 5,385,650 A | 1/1995 | Howarth et al. |
| 5,385,718 A | 1/1995 | Casci et al. |
| 5,395,981 A | 3/1995 | Marker |
| 5,399,258 A | 3/1995 | Fletcher et al. |
| 5,401,890 A | 3/1995 | Parks |
| 5,401,894 A | 3/1995 | Brasier et al. |
| 5,406,017 A | 4/1995 | Withers, Jr. |
| 5,411,641 A | 5/1995 | Trainham, III et al. |
| 5,414,173 A | 5/1995 | Garces et al. |
| 5,430,210 A | 7/1995 | Grasselli et al. |
| 5,430,214 A | 7/1995 | Smith et al. |
| 5,430,219 A | 7/1995 | Sanfilippo et al. |
| 5,433,828 A | 7/1995 | van Velzen et al. |
| 5,436,378 A | 7/1995 | Masini et al. |
| 5,444,168 A | 8/1995 | Brown |
| 5,446,234 A | 8/1995 | Casci et al. |
| 5,453,557 A | 9/1995 | Harley et al. |
| 5,456,822 A | 10/1995 | Marcilly et al. |
| 5,457,255 A | 10/1995 | Kumata et al. |
| 5,464,799 A | 11/1995 | Casci et al. |
| 5,465,699 A | 11/1995 | Voigt |
| 5,470,377 A | 11/1995 | Whitlock |
| 5,480,629 A | 1/1996 | Thompson et al. |
| 5,486,627 A | 1/1996 | Quarderer, Jr. et al. |
| 5,489,719 A | 2/1996 | Le et al. |
| 5,489,727 A | 2/1996 | Randolph et al. |

(56) References Cited

U.S. PATENT DOCUMENTS

| | | |
|---|---|---|
| 5,500,297 A | 3/1996 | Thompson et al. |
| 5,510,525 A | 4/1996 | Sen et al. |
| 5,523,503 A | 6/1996 | Funk et al. |
| 5,525,230 A | 6/1996 | Wrigley et al. |
| 5,538,540 A | 7/1996 | Whitlock |
| 5,563,313 A | 10/1996 | Chung et al. |
| 5,565,092 A | 10/1996 | Pannell et al. |
| 5,565,616 A | 10/1996 | Li et al. |
| 5,571,762 A | 11/1996 | Clerici et al. |
| 5,571,885 A | 11/1996 | Chung et al. |
| 5,599,381 A | 2/1997 | Whitlock |
| 5,600,043 A | 2/1997 | Johnston et al. |
| 5,600,045 A | 2/1997 | Van Der Aalst et al. |
| 5,609,654 A | 3/1997 | Le et al. |
| 5,633,419 A | 5/1997 | Spencer et al. |
| 5,639,930 A | 6/1997 | Penick |
| 5,653,956 A | 8/1997 | Zones |
| 5,656,149 A | 8/1997 | Zones et al. |
| 5,661,097 A | 8/1997 | Spencer et al. |
| 5,663,465 A | 9/1997 | Clegg et al. |
| 5,663,474 A | 9/1997 | Pham et al. |
| 5,674,464 A | 10/1997 | Van Velzen et al. |
| 5,675,046 A | 10/1997 | Ohno et al. |
| 5,675,052 A | 10/1997 | Menon et al. |
| 5,679,134 A | 10/1997 | Brugerolle et al. |
| 5,679,879 A | 10/1997 | Mercier et al. |
| 5,684,213 A | 11/1997 | Nemphos et al. |
| 5,693,191 A | 12/1997 | Pividal et al. |
| 5,695,890 A | 12/1997 | Thompson et al. |
| 5,698,747 A | 12/1997 | Godwin et al. |
| 5,705,712 A | 1/1998 | Frey et al. |
| 5,705,728 A | 1/1998 | Viswanathan et al. |
| 5,705,729 A | 1/1998 | Huang |
| 5,708,246 A | 1/1998 | Camaioni et al. |
| 5,720,858 A | 2/1998 | Noceti et al. |
| 5,728,897 A | 3/1998 | Buysch et al. |
| 5,728,905 A | 3/1998 | Clegg et al. |
| 5,734,073 A | 3/1998 | Chambers et al. |
| 5,741,949 A | 4/1998 | Mack |
| 5,744,669 A | 4/1998 | Kalnes et al. |
| 5,750,801 A | 5/1998 | Buysch et al. |
| 5,770,175 A | 6/1998 | Zones |
| 5,776,871 A | 7/1998 | Cothran et al. |
| 5,780,703 A | 7/1998 | Chang et al. |
| 5,782,936 A | 7/1998 | Riley |
| 5,798,314 A | 8/1998 | Spencer et al. |
| 5,814,715 A | 9/1998 | Chen et al. |
| 5,817,904 A | 10/1998 | Vic et al. |
| 5,821,394 A | 10/1998 | Schoebrechts et al. |
| 5,847,224 A | 12/1998 | Koga et al. |
| 5,849,978 A | 12/1998 | Benazzi et al. |
| 5,866,735 A | 2/1999 | Cheung et al. |
| 5,882,614 A | 3/1999 | Taylor, Jr. et al. |
| 5,895,831 A | 4/1999 | Brasier et al. |
| 5,898,086 A | 4/1999 | Harris |
| 5,905,169 A | 5/1999 | Jacobson |
| 5,906,892 A | 5/1999 | Thompson et al. |
| 5,908,963 A | 6/1999 | Voss et al. |
| 5,928,488 A | 7/1999 | Newman |
| 5,952,538 A | 9/1999 | Vaughn et al. |
| 5,959,170 A | 9/1999 | Withers, Jr. |
| 5,968,236 A | 10/1999 | Bassine |
| 5,969,195 A | 10/1999 | Stabel et al. |
| 5,977,402 A | 11/1999 | Sekiguchi et al. |
| 5,983,476 A | 11/1999 | Eshelman et al. |
| 5,986,158 A | 11/1999 | Van Broekhoven et al. |
| 5,994,604 A | 11/1999 | Reagen et al. |
| 5,998,679 A | 12/1999 | Miller et al. |
| 5,998,686 A | 12/1999 | Clem et al. |
| 6,002,059 A | 12/1999 | Hellring et al. |
| 6,015,867 A | 1/2000 | Fushimi et al. |
| 6,018,088 A | 1/2000 | Olah |
| 6,022,929 A | 2/2000 | Chen et al. |
| 6,034,288 A | 3/2000 | Scott et al. |
| 6,056,804 A | 5/2000 | Keefer et al. |
| 6,068,679 A | 5/2000 | Zheng |
| 6,072,091 A | 6/2000 | Cosyns et al. |
| 6,087,294 A | 7/2000 | Klabunde et al. |
| 6,090,312 A | 7/2000 | Ziaka et al. |
| 6,093,306 A | 7/2000 | Hanrahan et al. |
| 6,096,932 A | 8/2000 | Subramanian |
| 6,096,933 A | 8/2000 | Cheung et al. |
| 6,103,215 A | 8/2000 | Zones et al. |
| 6,107,561 A | 8/2000 | Thompson et al. |
| 6,117,371 A | 9/2000 | Mack |
| 6,124,514 A | 9/2000 | Emmrich et al. |
| 6,127,588 A | 10/2000 | Kimble et al. |
| 6,130,260 A | 10/2000 | Hall et al. |
| 6,143,939 A | 11/2000 | Farcasiu et al. |
| 6,169,218 B1 | 1/2001 | Hearn et al. |
| 6,180,841 B1 | 1/2001 | Fatutto et al. |
| 6,187,871 B1 | 2/2001 | Thompson et al. |
| 6,187,983 B1 | 2/2001 | Sun |
| 6,203,712 B1 | 3/2001 | Bronner et al. |
| 6,207,864 B1 | 3/2001 | Henningsen et al. |
| 6,225,517 B1 | 5/2001 | Nascimento et al. |
| 6,248,218 B1 | 6/2001 | Linkous et al. |
| 6,265,505 B1 | 7/2001 | McConville et al. |
| 6,281,405 B1 | 8/2001 | Davis et al. |
| 6,320,085 B1 | 11/2001 | Arvai et al. |
| 6,337,063 B1 | 1/2002 | Rouleau et al. |
| 6,342,200 B1 | 1/2002 | Rouleau et al. |
| 6,368,490 B1 | 4/2002 | Gestermann |
| 6,369,283 B1 | 4/2002 | Guram et al. |
| 6,372,949 B1 | 4/2002 | Brown et al. |
| 6,376,731 B1 | 4/2002 | Evans et al. |
| 6,380,328 B1 | 4/2002 | McConville et al. |
| 6,380,423 B2 | 4/2002 | Banning et al. |
| 6,380,444 B1 | 4/2002 | Bjerrum et al. |
| 6,395,945 B1 | 5/2002 | Randolph |
| 6,403,840 B1 | 6/2002 | Zhou et al. |
| 6,406,523 B1 | 6/2002 | Connor et al. |
| 6,423,211 B1 | 7/2002 | Randolph et al. |
| 6,426,441 B1 | 7/2002 | Randolph et al. |
| 6,426,442 B1 | 7/2002 | Ichikawa et al. |
| 6,452,058 B1 | 9/2002 | Schweizer et al. |
| 6,455,650 B1 | 9/2002 | Lipian et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,345 B2 | 10/2002 | Hintermann et al. |
| 6,472,572 B1 | 10/2002 | Zhou et al. |
| 6,475,463 B1 | 11/2002 | Elomari et al. |
| 6,475,464 B1 | 11/2002 | Rouleau et al. |
| 6,479,705 B2 | 11/2002 | Murata et al. |
| 6,482,997 B2 | 11/2002 | Petit-Clair et al. |
| 6,486,368 B1 | 11/2002 | Zhou et al. |
| 6,491,809 B1 | 12/2002 | Briot et al. |
| 6,495,484 B1 | 12/2002 | Holtcamp |
| 6,509,485 B2 | 1/2003 | Mul et al. |
| 6,511,526 B2 | 1/2003 | Jagger et al. |
| 6,514,319 B2 | 2/2003 | Keefer et al. |
| 6,518,474 B1 | 2/2003 | Sanderson et al. |
| 6,518,476 B1 | 2/2003 | Culp et al. |
| 6,525,228 B2 | 2/2003 | Chauvin et al. |
| 6,525,230 B2 | 2/2003 | Grosso |
| 6,528,693 B1 | 3/2003 | Gandy et al. |
| 6,538,162 B2 | 3/2003 | Chang et al. |
| 6,540,905 B1 | 4/2003 | Elomari |
| 6,545,191 B1 | 4/2003 | Stauffer |
| 6,547,958 B1 | 4/2003 | Elomari |
| 6,548,040 B1 | 4/2003 | Rouleau et al. |
| 6,552,241 B1 | 4/2003 | Randolph et al. |
| 6,566,572 B2 | 5/2003 | Okamoto et al. |
| 6,572,829 B2 | 6/2003 | Linkous et al. |
| 6,585,953 B2 | 7/2003 | Roberts et al. |
| 6,616,830 B2 | 9/2003 | Elomari |
| 6,620,757 B2 | 9/2003 | McConville et al. |
| 6,627,777 B2 | 9/2003 | Rossi et al. |
| 6,632,971 B2 | 10/2003 | Brown et al. |
| 6,635,793 B2 | 10/2003 | Mul et al. |
| 6,641,644 B2 | 11/2003 | Jagger et al. |
| 6,646,102 B2 | 11/2003 | Boriack et al. |
| 6,669,846 B2 | 12/2003 | Perriello |

(56) References Cited

U.S. PATENT DOCUMENTS

| | | |
|---|---|---|
| 6,672,572 B2 | 1/2004 | Werlen |
| 6,679,986 B1 | 1/2004 | Da Silva et al. |
| 6,680,415 B1 | 1/2004 | Gulotty, Jr. et al. |
| 6,692,626 B2 | 2/2004 | Keefer et al. |
| 6,692,723 B2 | 2/2004 | Rouleau et al. |
| 6,710,213 B2 | 3/2004 | Aoki et al. |
| 6,713,087 B2 | 3/2004 | Tracy et al. |
| 6,713,655 B2 | 3/2004 | Yilmaz et al. |
| RE38,493 E | 4/2004 | Keefer et al. |
| 6,723,808 B2 | 4/2004 | Holtcamp |
| 6,727,400 B2 | 4/2004 | Messier et al. |
| 6,740,146 B2 | 5/2004 | Simonds |
| 6,753,390 B2 | 6/2004 | Ehrman et al. |
| 6,765,120 B2 | 7/2004 | Weber et al. |
| 6,797,845 B1 | 9/2004 | Hickman et al. |
| 6,797,851 B2 | 9/2004 | Martens et al. |
| 6,821,924 B2 | 11/2004 | Gulotty, Jr. et al. |
| 6,822,123 B2 | 11/2004 | Stauffer |
| 6,822,125 B2 | 11/2004 | Lee et al. |
| 6,825,307 B2 | 11/2004 | Goodall |
| 6,825,383 B1 | 11/2004 | Dewkar et al. |
| 6,831,032 B2 | 12/2004 | Spaether |
| 6,838,576 B1 | 1/2005 | Wicki et al. |
| 6,841,063 B2 | 1/2005 | Elomari |
| 6,852,896 B2 | 2/2005 | Stauffer |
| 6,866,950 B2 | 3/2005 | Connor et al. |
| 6,869,903 B2 | 3/2005 | Matsunaga |
| 6,875,339 B2 | 4/2005 | Rangarajan et al. |
| 6,878,853 B2 | 4/2005 | Tanaka et al. |
| 6,888,013 B2 | 5/2005 | Paparatto et al. |
| 6,900,363 B2 | 5/2005 | Harth et al. |
| 6,902,602 B2 | 6/2005 | Keefer et al. |
| 6,903,171 B2 | 6/2005 | Rhodes et al. |
| 6,909,024 B1 | 6/2005 | Jones et al. |
| 6,921,597 B2 | 7/2005 | Keefer et al. |
| 6,933,417 B1 | 8/2005 | Henley et al. |
| 6,946,566 B2 | 9/2005 | Yaegashi et al. |
| 6,953,868 B2 | 10/2005 | Boaen et al. |
| 6,953,870 B2 | 10/2005 | Yan et al. |
| 6,953,873 B2 | 10/2005 | Cortright et al. |
| 6,956,140 B2 | 10/2005 | Ehrenfeld |
| 6,958,306 B2 | 10/2005 | Holtcamp |
| 6,984,763 B2 | 1/2006 | Schweizer et al. |
| 7,001,872 B2 | 2/2006 | Pyecroft et al. |
| 7,002,050 B2 | 2/2006 | Santiago Fernandez et al. |
| 7,011,811 B2 | 3/2006 | Elomari |
| 7,019,182 B2 | 3/2006 | Grosso |
| 7,026,145 B2 | 4/2006 | Mizrahi et al. |
| 7,026,519 B2 | 4/2006 | Santiago Fernandez et al. |
| 7,037,358 B2 | 5/2006 | Babicki et al. |
| 7,045,111 B1 | 5/2006 | DeGroot et al. |
| 7,045,670 B2 | 5/2006 | Johnson et al. |
| 7,049,388 B2 | 5/2006 | Boriack et al. |
| 7,053,252 B2 | 5/2006 | Boussand et al. |
| 7,057,081 B2 | 6/2006 | Allison et al. |
| 7,060,865 B2 | 6/2006 | Ding et al. |
| 7,064,238 B2 | 6/2006 | Waycuilis |
| 7,064,240 B2 | 6/2006 | Ohno et al. |
| 7,067,448 B1 | 6/2006 | Weitkamp et al. |
| 7,083,714 B2 | 8/2006 | Elomari |
| 7,084,308 B1 | 8/2006 | Stauffer |
| 7,091,270 B2 | 8/2006 | Zilberman et al. |
| 7,091,387 B2 | 8/2006 | Fong et al. |
| 7,091,391 B2 | 8/2006 | Stauffer |
| 7,094,936 B1 | 8/2006 | Owens et al. |
| 7,098,371 B2 | 8/2006 | Mack et al. |
| 7,105,710 B2 | 9/2006 | Boons et al. |
| 7,138,534 B2 | 11/2006 | Forlin et al. |
| 7,141,708 B2 | 11/2006 | Marsella et al. |
| 7,145,045 B2 | 12/2006 | Harmsen et al. |
| 7,148,356 B2 | 12/2006 | Smith, III et al. |
| 7,148,390 B2 | 12/2006 | Zhou et al. |
| 7,151,199 B2 | 12/2006 | Martens et al. |
| 7,161,050 B2 | 1/2007 | Sherman et al. |
| 7,169,730 B2 | 1/2007 | Ma et al. |
| 7,176,340 B2 | 2/2007 | Van Broekhoven et al. |
| 7,176,342 B2 | 2/2007 | Bellussi et al. |
| 7,182,871 B2 | 2/2007 | Perriello |
| 7,193,093 B2 | 3/2007 | Murray et al. |
| 7,196,239 B2 | 3/2007 | Van Egmond et al. |
| 7,199,083 B2 | 4/2007 | Zevallos |
| 7,199,255 B2 | 4/2007 | Murray et al. |
| 7,208,641 B2 | 4/2007 | Nagasaki et al. |
| 7,214,750 B2 | 5/2007 | McDonald et al. |
| 7,220,391 B1 | 5/2007 | Huang et al. |
| 7,226,569 B2 | 6/2007 | Elomari |
| 7,226,576 B2 | 6/2007 | Elomari |
| 7,230,150 B2 | 6/2007 | Grosso et al. |
| 7,230,151 B2 | 6/2007 | Martens et al. |
| 7,232,872 B2 | 6/2007 | Shaffer et al. |
| 7,238,846 B2 | 7/2007 | Janssen et al. |
| 7,244,795 B2 | 7/2007 | Agapiou et al. |
| 7,244,867 B2 | 7/2007 | Waycuilis |
| 7,250,107 B2 | 7/2007 | Benazzi et al. |
| 7,250,542 B2 | 7/2007 | Smith, Jr. et al. |
| 7,252,920 B2 | 8/2007 | Kurokawa et al. |
| 7,253,327 B2 | 8/2007 | Janssens et al. |
| 7,253,328 B2 | 8/2007 | Stauffer |
| 7,265,193 B2 | 9/2007 | Weng et al. |
| 7,267,758 B2 | 9/2007 | Benazzi et al. |
| 7,268,263 B1 | 9/2007 | Frey et al. |
| 7,271,303 B1 | 9/2007 | Sechrist et al. |
| 7,273,957 B2 | 9/2007 | Bakshi et al. |
| 7,282,603 B2 | 10/2007 | Richards |
| 7,285,698 B2 | 10/2007 | Liu et al. |
| 7,304,193 B1 | 12/2007 | Frey et al. |
| 7,342,144 B2 | 3/2008 | Kaizik et al. |
| 7,348,295 B2 | 3/2008 | Zones et al. |
| 7,348,464 B2 | 3/2008 | Waycuilis |
| 7,357,904 B2 | 4/2008 | Zones et al. |
| 7,361,794 B2 | 4/2008 | Grosso |
| 7,365,102 B1 | 4/2008 | Weissman |
| 7,390,395 B2 | 6/2008 | Elomari |
| 7,560,607 B2 | 7/2009 | Waycuilis |
| 7,674,941 B2 | 3/2010 | Waycuilis et al. |
| 7,713,510 B2 | 5/2010 | Harrod et al. |
| 7,880,041 B2 | 2/2011 | Waycuilis |
| 8,008,535 B2 | 8/2011 | Waycuilis |
| 8,173,851 B2 | 5/2012 | Waycuilis et al. |
| 8,198,495 B2 | 6/2012 | Waycuilis et al. |
| 8,232,441 B2 | 7/2012 | Waycuilis |
| 8,282,810 B2 | 10/2012 | Waycuilis |
| 8,367,884 B2 | 2/2013 | Waycuilis |
| 8,373,015 B2 | 2/2013 | Stark et al. |
| 8,415,517 B2 | 4/2013 | Gadewar et al. |
| 8,436,220 B2 * | 5/2013 | Kurukchi et al. ............ 585/310 |
| 8,449,849 B2 | 5/2013 | Gadewar et al. |
| 8,642,822 B2 | 2/2014 | Brickey et al. |
| 2001/0051662 A1 | 12/2001 | Arcuri et al. |
| 2002/0102672 A1 | 8/2002 | Mizrahi |
| 2002/0193649 A1 | 12/2002 | O'Rear et al. |
| 2002/0198416 A1 | 12/2002 | Zhou et al. |
| 2003/0004380 A1 | 1/2003 | Grumann |
| 2003/0065239 A1 | 4/2003 | Zhu |
| 2003/0069452 A1 | 4/2003 | Sherman et al. |
| 2003/0078456 A1 | 4/2003 | Yilmaz et al. |
| 2003/0120121 A1 | 6/2003 | Sherman et al. |
| 2003/0125589 A1 | 7/2003 | Grosso |
| 2003/0166973 A1 | 9/2003 | Zhou et al. |
| 2004/0006246 A1 | 1/2004 | Sherman et al. |
| 2004/0055955 A1 | 3/2004 | Davis |
| 2004/0062705 A1 | 4/2004 | Leduc |
| 2004/0152929 A1 | 8/2004 | Clarke |
| 2004/0158107 A1 | 8/2004 | Aoki |
| 2004/0158108 A1 | 8/2004 | Snoble |
| 2004/0171779 A1 | 9/2004 | Matyjaszewski et al. |
| 2004/0187684 A1 | 9/2004 | Elomari |
| 2004/0188271 A1 | 9/2004 | Ramachandraiah et al. |
| 2004/0188324 A1 | 9/2004 | Elomari |
| 2004/0220433 A1 | 11/2004 | Van Der Heide |
| 2005/0027084 A1 | 2/2005 | Clarke |
| 2005/0038310 A1 | 2/2005 | Lorkovic et al. |
| 2005/0042159 A1 | 2/2005 | Elomari |
| 2005/0047927 A1 | 3/2005 | Lee et al. |

(56) References Cited

U.S. PATENT DOCUMENTS

| | | |
|---|---|---|
| 2005/0148805 A1 | 7/2005 | Jones |
| 2005/0171393 A1 | 8/2005 | Lorkovic |
| 2005/0192468 A1 | 9/2005 | Sherman et al. |
| 2005/0215837 A1 | 9/2005 | Hoffpauir |
| 2005/0218041 A1 | 10/2005 | Yoshida et al. |
| 2005/0234276 A1 | 10/2005 | Waycuilis |
| 2005/0234277 A1 | 10/2005 | Waycuilis |
| 2005/0245771 A1 | 11/2005 | Fong et al. |
| 2005/0245772 A1 | 11/2005 | Fong |
| 2005/0245777 A1 | 11/2005 | Fong |
| 2005/0267224 A1 | 12/2005 | Herling |
| 2006/0025617 A1 | 2/2006 | Begley |
| 2006/0100469 A1 | 5/2006 | Waycuilis |
| 2006/0135823 A1 | 6/2006 | Jun |
| 2006/0138025 A1 | 6/2006 | Zones |
| 2006/0138026 A1 | 6/2006 | Chen |
| 2006/0149116 A1 | 7/2006 | Slaugh |
| 2006/0229228 A1 | 10/2006 | Komon et al. |
| 2006/0229475 A1 | 10/2006 | Weiss et al. |
| 2006/0270863 A1 | 11/2006 | Reiling |
| 2006/0288690 A1 | 12/2006 | Elomari |
| 2007/0004955 A1 | 1/2007 | Kay |
| 2007/0078285 A1 | 4/2007 | Dagle |
| 2007/0100189 A1 | 5/2007 | Stauffer |
| 2007/0129584 A1 | 6/2007 | Basset |
| 2007/0142680 A1 | 6/2007 | Ayoub |
| 2007/0148067 A1 | 6/2007 | Zones |
| 2007/0148086 A1 | 6/2007 | Zones |
| 2007/0149778 A1 | 6/2007 | Zones |
| 2007/0149789 A1 | 6/2007 | Zones |
| 2007/0149819 A1 | 6/2007 | Zones |
| 2007/0149824 A1 | 6/2007 | Zones |
| 2007/0149837 A1 | 6/2007 | Zones |
| 2007/0149838 A1 | 6/2007 | Chretien |
| 2007/0197801 A1 | 8/2007 | Bolk |
| 2007/0197847 A1 | 8/2007 | Liu |
| 2007/0213545 A1 | 9/2007 | Bolk |
| 2007/0238905 A1 | 10/2007 | Arredondo |
| 2007/0238909 A1* | 10/2007 | Gadewar et al. ............. 585/16 |
| 2007/0276168 A1 | 11/2007 | Garel |
| 2007/0284284 A1 | 12/2007 | Zones |
| 2008/0022717 A1 | 1/2008 | Yoshida et al. |
| 2008/0152555 A1 | 6/2008 | Wang et al. |
| 2008/0171898 A1 | 7/2008 | Waycuilis |
| 2008/0183022 A1 | 7/2008 | Waycuilis |
| 2008/0188697 A1 | 8/2008 | Lorkovic |
| 2008/0200740 A1 | 8/2008 | Waycuilis |
| 2008/0210596 A1 | 9/2008 | Litt et al. |
| 2008/0275279 A1 | 11/2008 | Podkolzin et al. |
| 2008/0275284 A1 | 11/2008 | Waycuilis |
| 2008/0314758 A1 | 12/2008 | Grosso et al. |
| 2009/0005620 A1 | 1/2009 | Waycuilis et al. |
| 2009/0163749 A1 | 6/2009 | Li et al. |
| 2009/0247796 A1 | 10/2009 | Waycuilis et al. |
| 2009/0270655 A1 | 10/2009 | Fong et al. |
| 2009/0306443 A1 | 12/2009 | Stark et al. |
| 2009/0308759 A1 | 12/2009 | Waycuilis |
| 2009/0312586 A1 | 12/2009 | Waycuilis et al. |
| 2009/0326292 A1 | 12/2009 | Waycuilis |
| 2010/0030005 A1 | 2/2010 | Sauer et al. |
| 2010/0087686 A1 | 4/2010 | Fong et al. |
| 2010/0096588 A1 | 4/2010 | Gadewar et al. |
| 2010/0099929 A1 | 4/2010 | Gadewar et al. |
| 2010/0099930 A1 | 4/2010 | Stoimenov et al. |
| 2010/0105972 A1 | 4/2010 | Lorkovic |
| 2010/0234637 A1 | 9/2010 | Fong et al. |
| 2010/0270167 A1 | 10/2010 | McFarland |
| 2011/0015458 A1 | 1/2011 | Waycuilis et al. |
| 2011/0071326 A1 | 3/2011 | Waycuilis |
| 2011/0198285 A1 | 8/2011 | Wallace |
| 2011/0218372 A1 | 9/2011 | Waycuilis et al. |
| 2011/0218374 A1 | 9/2011 | Waycuilis |
| 2012/0141356 A1 | 6/2012 | Brickey et al. |
| 2012/0245399 A1 | 9/2012 | Kurukchi et al. |
| 2012/0313034 A1 | 12/2012 | Kurukchi et al. |
| 2013/0046121 A1 | 2/2013 | Kurukchi et al. |
| 2013/0079564 A1 | 3/2013 | Waycuilis |
| 2013/0090504 A1 | 4/2013 | Roscoe et al. |
| 2013/0102820 A1 | 4/2013 | Waycuilis et al. |
| 2013/0102821 A1 | 4/2013 | Waycuilis et al. |
| 2013/0156681 A1 | 6/2013 | Kurukchi et al. |
| 2013/0158324 A1 | 6/2013 | Waycuilis et al. |
| 2013/0178675 A1 | 7/2013 | Kurukchi et al. |
| 2013/0217938 A1 | 8/2013 | Waycuilis et al. |

FOREIGN PATENT DOCUMENTS

| | | |
|---|---|---|
| CA | 1202610 | 4/1986 |
| CA | 2542857 | 5/2005 |
| CA | 2236126 | 8/2006 |
| CA | 2203115 | 9/2006 |
| CA | 2510093 | 12/2006 |
| CA | 2641348 A1 | 8/2007 |
| CA | 2684765 A1 | 11/2008 |
| EP | 0164798 A1 | 12/1985 |
| EP | 0418971 A1 | 3/1991 |
| EP | 0418974 A1 | 3/1991 |
| EP | 0418975 A1 | 3/1991 |
| EP | 0510238 A1 | 10/1992 |
| EP | 0526908 A2 | 2/1993 |
| EP | 0346612 B1 | 8/1993 |
| EP | 0560546 A1 | 9/1993 |
| EP | 0976705 A1 | 2/2000 |
| EP | 1186591 A2 | 3/2002 |
| EP | 1253126 A1 | 10/2002 |
| EP | 1312411 A2 | 5/2003 |
| EP | 1235769 B1 | 5/2004 |
| EP | 1435349 A2 | 7/2004 |
| EP | 1440939 A1 | 7/2004 |
| EP | 1235772 B1 | 1/2005 |
| EP | 1661620 A1 | 5/2006 |
| EP | 1760057 A1 | 3/2007 |
| EP | 1689728 B1 | 4/2007 |
| EP | 1808227 A1 | 7/2007 |
| EP | 1837320 A1 | 9/2007 |
| GB | 5125 | 0/1912 |
| GB | 156122 | 3/1922 |
| GB | 294100 | 6/1929 |
| GB | 363009 | 12/1931 |
| GB | 402928 | 12/1933 |
| GB | 474922 A | 11/1937 |
| GB | 536491 | 5/1941 |
| GB | 553950 | 6/1943 |
| GB | 586483 | 3/1947 |
| GB | 775590 | 5/1957 |
| GB | 793214 | 4/1958 |
| GB | 796048 | 6/1958 |
| GB | 796085 | 6/1958 |
| GB | 883256 A | 11/1961 |
| GB | 930341 A | 7/1963 |
| GB | 950975 | 3/1964 |
| GB | 950976 | 3/1964 |
| GB | 991303 | 5/1965 |
| GB | 995960 | 6/1965 |
| GB | 1015033 | 12/1965 |
| GB | 1104294 | 2/1968 |
| GB | 1133752 | 11/1968 |
| GB | 1172002 | 11/1969 |
| GB | 1212240 | 11/1970 |
| GB | 1233299 | 5/1971 |
| GB | 1253618 | 11/1971 |
| GB | 1263806 | 2/1972 |
| GB | 1446803 | 8/1976 |
| GB | 1542112 | 3/1979 |
| GB | 2095243 A | 9/1982 |
| GB | 2095245 A | 9/1982 |
| GB | 2095249 A | 9/1982 |
| GB | 2116546 A | 9/1982 |
| GB | 2120249 A | 11/1983 |
| GB | 2185754 A | 7/1987 |
| GB | 2191214 A | 12/1987 |
| SU | 694483 A1 | 10/1979 |
| WO | 83/00859 | 3/1983 |
| WO | 85/04863 | 11/1985 |

(56) References Cited

FOREIGN PATENT DOCUMENTS

| | | |
|---|---|---|
| WO | 85/04867 | 11/1985 |
| WO | 90/08120 | 7/1990 |
| WO | 90/08752 | 8/1990 |
| WO | 91/18856 | 12/1991 |
| WO | 92/03401 | 3/1992 |
| WO | 92/12946 | 8/1992 |
| WO | 93/06039 A1 | 4/1993 |
| WO | 93/16798 | 9/1993 |
| WO | 96/22263 | 7/1996 |
| WO | 97/44302 | 11/1997 |
| WO | 98/12165 | 3/1998 |
| WO | 99/07443 | 2/1999 |
| WO | 00/07718 A1 | 2/2000 |
| WO | 00/09261 A1 | 2/2000 |
| WO | 01/14300 A1 | 3/2001 |
| WO | 01/38275 A1 | 5/2001 |
| WO | 01/44149 A1 | 6/2001 |
| WO | 02/094749 A1 | 11/2002 |
| WO | 02/094750 A1 | 11/2002 |
| WO | 02/094751 A2 | 11/2002 |
| WO | 02/094752 A1 | 11/2002 |
| WO | 03/000635 A1 | 1/2003 |
| WO | 03/002251 A2 | 1/2003 |
| WO | 03/018524 A1 | 3/2003 |
| WO | 03/020676 A1 | 3/2003 |
| WO | 03/022827 A1 | 3/2003 |
| WO | 03/043575 A2 | 5/2003 |
| WO | 03/051813 A1 | 6/2003 |
| WO | 03/062143 A1 | 7/2003 |
| WO | 03/062172 A2 | 7/2003 |
| WO | 03/078366 A1 | 9/2003 |
| WO | 2004/018093 A2 | 3/2004 |
| WO | 2004/067487 A2 | 8/2004 |
| WO | 2005/014168 A1 | 2/2005 |
| WO | 2005/019143 A1 | 3/2005 |
| WO | 2005/021468 A1 | 3/2005 |
| WO | 2005/035121 A2 | 4/2005 |
| WO | 2005/037758 A1 | 4/2005 |
| WO | 2005/054120 A2 | 6/2005 |
| WO | 2005/056525 A2 | 6/2005 |
| WO | 2005/058782 A1 | 6/2005 |
| WO | 2005/090272 A1 | 9/2005 |
| WO | 2005/095310 A2 | 10/2005 |
| WO | 2005/104689 A2 | 11/2005 |
| WO | 2005/105709 A1 | 11/2005 |
| WO | 2005/105715 A1 | 11/2005 |
| WO | 2005/110953 A1 | 11/2005 |
| WO | 2005/113437 A1 | 12/2005 |
| WO | 2005/113440 A1 | 12/2005 |
| WO | 2006/007093 A1 | 1/2006 |
| WO | 2006/015824 A1 | 2/2006 |
| WO | 2006/019399 A2 | 2/2006 |
| WO | 2006/020234 A1 | 2/2006 |
| WO | 2006/036293 A1 | 4/2006 |
| WO | 2006/039213 A1 | 4/2006 |
| WO | 2006/039354 A2 | 4/2006 |
| WO | 2006/043075 A1 | 4/2006 |
| WO | 2006/053345 A1 | 5/2006 |
| WO | 2006/067155 A2 | 6/2006 |
| WO | 2006/067188 A1 | 6/2006 |
| WO | 2006/067190 A1 | 6/2006 |
| WO | 2006/067191 A1 | 6/2006 |
| WO | 2006/067192 A1 | 6/2006 |
| WO | 2006/067193 A1 | 6/2006 |
| WO | 2006/069107 A2 | 6/2006 |
| WO | 2006/071354 A1 | 7/2006 |
| WO | 2006/083427 A2 | 8/2006 |
| WO | 2006/100312 A1 | 9/2006 |
| WO | 2006/104909 A2 | 10/2006 |
| WO | 2006/104914 A1 | 10/2006 |
| WO | 2006/111997 A1 | 10/2006 |
| WO | 2006/113205 A2 | 10/2006 |
| WO | 2006/118935 A2 | 11/2006 |
| WO | 2007/001934 A2 | 1/2007 |
| WO | 2007/017900 A2 | 2/2007 |
| WO | 2007/044139 A1 | 4/2007 |
| WO | 2007/046986 A2 | 4/2007 |
| WO | 2007/050745 A1 | 5/2007 |
| WO | 2007/071046 A1 | 6/2007 |
| WO | 2007/079038 A2 | 7/2007 |
| WO | 2007/091009 A2 | 8/2007 |
| WO | 2007/094995 A2 | 8/2007 |
| WO | 2007/107031 A1 | 9/2007 |
| WO | 2007/111997 A2 | 10/2007 |
| WO | 2007/114479 A1 | 10/2007 |
| WO | 2007/125332 A1 | 11/2007 |
| WO | 2007/130054 A1 | 11/2007 |
| WO | 2007/130055 A1 | 11/2007 |
| WO | 2007/141295 A1 | 12/2007 |
| WO | 2007/142745 A1 | 12/2007 |
| WO | 2008/036562 A1 | 3/2008 |
| WO | 2008/036563 A2 | 3/2008 |
| WO | 2008/106318 A1 | 9/2008 |
| WO | 2008/106319 A1 | 9/2008 |
| WO | 2008/157043 A1 | 12/2008 |
| WO | 2008/157044 A1 | 12/2008 |
| WO | 2008/157045 A1 | 12/2008 |
| WO | 2008/157046 A1 | 12/2008 |
| WO | 2008/157047 A1 | 12/2008 |
| WO | 2009/152403 A1 | 12/2009 |
| WO | 2009/152405 A1 | 12/2009 |
| WO | 2009/152408 A1 | 12/2009 |
| WO | 2010/009376 A1 | 1/2010 |
| WO | 2011/008573 A1 | 1/2011 |
| WO | 2011/109244 A2 | 9/2011 |
| WO | 2011/159490 A1 | 12/2011 |

OTHER PUBLICATIONS

Abstract of CN 1199039, Pentanol and its production process, Publication date: Nov. 18, 1998, Inventor: Kailun, esp@cenet database—worldwide.

Abstract of CN 1210847, Process for producing low carbon alcohol by directly hydrating low carbon olefines, Publication date: Mar. 17, 1999, Inventor: Zhenguo et al., esp@cenet database—worldwide.

Abstract of CN 1321728, Method for preparing aromatic hydrocarbon and hydrogen gas by using law-pressure gas, Publication date: Nov. 14, 2001, Inventor: Jie et al., esp@cenet database—worldwide.

Abstract of CN 1451721, Process for non-catalytic combustion deoxidizing coal mine gas for producing methanol, Publication date: Oct. 29, 2003, Inventor: Pengwan et al., esp@cenet database—worldwide.

Abstract of CN 1623969, Method for preparing 1, 4-benzene dimethanol, Publication date: Jun. 8, 2005, Inventor: Jiarong et al., esp@cenet database—worldwide.

Abstract of CN 1657592, Method for converting oil to multiple energy fuel product, Publication date: Aug. 24, 2005, Inventor: Li, esp@cenet database—worldwide.

Abstract of CN 1687316, Method for producing biologic diesel oil from rosin, Publication date: Oct. 26, 2005, Inventor: Jianchun et al., esp@cenet database—worldwide.

Abstract of CN 1696248, Method for synthesizing biologic diesel oil based on ion liquid, Publication date: Nov. 16, 2005, Inventor: Sun, esp@cenet database—worldwide.

Abstract of CN 1699516, Process for preparing bio-diesel-oil by using miroalgae fat, Publication date: Nov. 23, 2005, Inventor: Miao, esp@cenet database—worldwide.

Abstract of CN 1704392, Process for producing alkylbenzene, Publication date: Dec. 7, 2005, Inventor: Gao, esp@cenet database—worldwide.

Abstract of CN 1724612, Biological diesel oil catalyst and method of synthesizing biological diesel oil using sai catalyst, Publication date: Jan. 25, 2006, Inventor: Gu, esp@cenet database—worldwide.

Abstract of CN 1986737, Process for producing biodiesel oil with catering waste oil, Publication date: Jun. 27, 2007, Inventor: Chen, esp@cenet database—worldwide.

Abstract of CN 100999680, Esterification reaction tech. of preparing biodiesel by waste oil, Publication date: Jul. 18, 2007, Inventor: Weiming, esp@cenet database—worldwide.

Abstract of CN 101016229, Refining method for bromomeoamyl alcohol, Publication date: Aug. 15, 2007, Inventor: Tian, esp@cenet database—worldwide.

(56) References Cited

OTHER PUBLICATIONS

Abstract of DE 3209964, Process for the preparation of chlorinated hydrocarbons, Publication date: Nov. 11, 1982, Inventor: Pyke et al., esp@cenet database—worldwide.
Abstract of DE 3210196, Process for the preparation of a monochlorinated olefin, Publication date: Jan. 5, 1983, Inventor: Pyke et al., esp@cenet database—worldwide.
Abstract of DE 3226028, Process for the preparation of monochlorinated olefin, Publication date: Feb. 3, 1983, Inventor: Pyke et al., esp@cenet database—worldwide.
Abstract of DE 3334225, Process for the preparation of 1,2-dichloroethane, Publication date: Apr. 4, 1985, Inventor: Hebgen et al., esp@cenet database—worldwide.
Abstract of DE 4232056, 2,5-Di:methyl-hexane-2,5-di:ol continuous prodn. from tert. butanol—by oxidative dimerisation in two phase system with vigorous stirring, using aq. phase with specified density to facilitate phase sepn., Publication date: Mar. 31, 1994, Inventor: Gnann et al., esp@cenet database—worldwide.
Abstract of DE 4434823, Continuous prodn. Of hydroxy-benzyl alkyl ether, Publication date: Apr. 4, 1996, Inventor: Stein et al., esp@cenet database—worldwide.
Abstract of EP 0021497 (A1), Synthesis of polyoxyalkylene glycol monoalkyl ethers., Publication date: Jan. 7, 1981, Inventor: Gibson, esp@cenet database—worldwide.
Abstract of EP 0039471, Process for the preparation of 2-chloro-1,1,1,2,3,3,3-heptafluoropropane., Publication date: Nov. 11, 1981, Inventor: Von Halasz, esp@cenet database—worldwide.
Abstract of EP 0101337, Process for the production of methylene chloride., Publication date: Feb. 22, 1984, Inventor: Olah et al., esp@cenet database—worldwide.
Abstract of EP 0235110, Process for the stabilization of silicalite catalysts., Publication date: Sep. 2, 1987, Inventor: Debras et al., esp@cenet database—worldwide.
Abstract of EP 0407989, Method for the production of 1,1,1-trifluoro-2,2-dichloroethane by photochlorination., Publication date: Jan. 16, 1991, Inventor: Cremer et al., esp@cenet database—worldwide.
Abstract of EP 0442258, Process for the preparation of a polyunsaturated olefin., Publication date: Aug. 21, 1991, Inventor: Gaudin et al., esp@cenet database, worldwide.
Abstract of EP 0465294, Process for the preparation of unsaturated bromides., Publication date: Jan. 8, 1992, Inventor: Decaudin et al., esp@cenet database—worldwide.
Abstract of EP 0549387, Synthesis of n-perfluorooctylbromide., Publication date: Jun. 30, 1993, Inventor: Drivon et al., esp@cenet database—worldwide.
Abstract of EP 0850906, Process and apparatus for the etherification of olefinic hydrocarbon feedstocks, Publication date: Jul. 1, 1998, Inventor: Masson, esp@cenet database—worldwide.
Abstract of EP 0858987, Process for conversion of lighter alkanes to higher hydrocarbons, Publication date: Aug. 19, 1998, Inventor: Amariglio, et al., esp@cenet database—worldwide.
Abstract of EP 1395536, Oxidative halogenation of C1 hydrocarbons to halogenated C1 hydrocarbons and integrated processes related thereto, Publication date: Mar. 10, 2004, Inventor: Schweizer et al., esp@cenet database—worldwide.
Abstract of EP 1404636, Integrated process for synthesizing alcohols and ethers from alkanes, Publication date: Apr. 7, 2004, Inventor: Zhou et al., esp@cenet database—worldwide.
Abstract of EP 1435349 A2, Integrated process for synthesizing alcohols and ethers from alkanes, Publication date: Jul. 7, 2004, Inventor: Zhou et al.
Abstract of EP 1474371, Integrated process for synthesizing alcohols, ethers, and olefins from alkanes, Publication date: Nov. 10, 2004, Inventor: Zhou et al., esp@cenet database—worldwide.
Abstract of FR 2692259, Aromatisation of 2-4C hydrocarbons—using a fixed-mobile-catalytic bed process, Publication date: Dec. 17, 1993, Inventor: Alario et al., esp@cenet database—worldwide.
Abstract of FR 2880019, Manufacturing 1,2-dichloroethane, comprises cracking core hydrocarbonated source, separating into fractions, sending into chlorination reaction chamber and oxychlorination reaction chamber and separating from chambers, Publication date: Jun. 30, 2006, Inventor: Strebelle et al., esp@cenet database—worldwide.
Abstract of FR 2883870, Formation of 1,2-dichloroethane useful in manufacture of vinyl chloride involves subjecting mixture of cracking products obtained by cracking of hydrocarbon source, to a succession of aqueous quenching, alkaline washing, and oxidation steps, Publication date: Oct. 6, 2006, Inventor: Balthasart et al., esp@cenet database—worldwide.
Abstract of FR 2883871, Preparing 1,2-dichloroethane comprises cracking hydrocarbon to form mixture, sending mixture into storage reservoir, supplying mixture into chlorination and/or oxychloration reactor, and separating 1,2-dichloroethane from reactor, Publication date: Oct. 6, 2006, Inventor: Balthasart et al., esp@cenet database—worldwide.
Abstract of IT 1255246, Process for the preparation of dinitrodiphenylmethanes, Publication date: Oct. 20, 1995, Applicant: Enichem Spa et al., esp@cenet database—worldwide.
Abstract of IT 1255358, Process for the synthesis of 1,4-butanediol, Publication date: Oct. 31, 1995, Inventor: Ricci Marco, esp@cenet database—worldwide.
Abstract of JP 2142740, Production of fluoroalcohol, Publication date: May 31, 1990, Inventor: Tsutomu et al., esp@cenet database—worldwide.
Abstract of JP 2144150, Chemical process and catalyst used therefore, Publication date: Jun. 1, 1990, Inventor: Deidamusu et al., esp@cenet database—worldwide.
Abstract of JP 4305542, Production of halogenated hydrocarbon compounds, Publication date: Oct. 28, 1992, Inventor: Shinsuke et al., esp@cenet database—worldwide.
Abstract of JP 6172225, Method for fluorinating halogenated hydrocarbon, Publication date: Jun. 21, 1994, Inventor: Takashi et al., esp@cenet database—worldwide.
Abstract of JP 6206834, Production of Tetrachloroethanes, Publication date: Jul. 26, 1994, Inventor: Toshiro et al., esp@cenet database—worldwide.
Abstract of JP 8266888, Method for decomposing aromatic halogen compound, Publication date: Oct. 15, 1996, Inventor: Yuuji et al., esp@cenet database—worldwide.
Abstract of JP 2001031605, Production of 3-hydroxy-1-cycloalkene, Publication date: Feb. 6, 2001, Inventor: Hideo et al., esp@cenet database—worldwide.
Abstract of JP 2004075683, Method for producing optically active halogenohydroxypropyl compound and glycidyl compound, Publication date: Mar. 11, 2004, Inventor: Keisuke et al., esp@cenet database—worldwide.
Abstract of JP 2004189655, Method for fluorinating with microwave, Publication date: Jul. 8, 2004, Inventor: Masaharu et al., esp@cenet database—worldwide.
Abstract of JP 2005075798, Method for producing adamantyl ester compound, Publication date: Mar. 24, 2005, Inventor: Norihiro et al., esp@cenet database—worldwide.
Abstract of JP 2005082563, Method for producing 1,3-adamantanediol, Publication date: Mar. 31, 2005, Inventor: Norihiro et al., esp@cenet database—worldwide.
Abstract of JP 2005145977, Process for catalytically oxidizing olefin and cycloolefin for the purpose of forming enol, olefin ketone, and epoxide, Publication date: Jun. 9, 2005, Inventor: Cancheng et al., esp@cenet database—worldwide.
Abstract of JP 2005254092, Method of manufacturing alkynes, Publication date: Sep. 22, 2005, Inventor: Shirakawa Eiji, esp@cenet database—worldwide.
Abstract of JP 2006151892, Preparation method of alcohol derivative, Publication date: Jun. 15, 2006, Inventor: Baba Akio et al., esp@cenet database—worldwide.
Abstract of JP 2006152263, Organic-inorganic hybrid-type mesoporous material, method for producing the same, and solid catalyst, Publication date: Jun. 15, 2006, Inventor: Junko et al., esp@cenet database—worldwide.

(56) References Cited

OTHER PUBLICATIONS

Abstract of JP 2006193473, Aryl polyadamantane derivative having carboxy or acid anhydride group and method for producing the same, Publication date: Jul. 27, 2006, Inventor: Yasuto et al, esp@cenet database—worldwide.
Abstract of JP 2006231318, Phosphorus containing macromolecule immobilizing palladium catalyst and method for using the same, Publication date: Sep. 7, 2006, Inventor: Osamu et al., esp@cenet database—worldwide.
Abstract of JP 2006263567, Optical resolution method of optical isomer and optical resolution device, Publication date: Oct. 5, 2006, Inventor: Yoshikazu et al., esp@cenet database—worldwide.
Abstract of JP 2006265157, Method for catalytically activating silicated nucleating agent using phosphazene base, Publication date: Oct. 5, 2006, Inventor: Yoshinori et al., esp@cenet database—worldwide.
Abstract of JP 2006306758, Method for producing biaryl compound, Publication date: Nov. 9, 2006, Inventor: Yuji et al., esp@cenet database—worldwide.
Abstract of JP 2007001942, Production method of para-xylene, Publication date: Jan. 11, 2007, Inventor: Kazuyoshi, esp@cenet database—worldwide.
Abstract of JP 2007015994, Method for synthesizing organic compound in ultra high rate under high temperature and high pressure water, and system of high temperature and high pressure reaction, Publication date: Jan. 25, 2007, Inventor: Hajime et al., esp@cenet database—worldwide.
Abstract of JP 2007045756, Hydrogenation method using diaphragm type hydrogenation catalyst, hydrogenation reaction apparatus and diaphragm type hydrogenation catalyst, Publication date: Feb. 22, 2007, Inventor: Shuji et al., esp@cenet database—worldwide.
Abstract of JP 2007061594, Method for decomposing organohalogen compound and mobile decomposition system, Publication date: Mar. 15, 2007, Inventor: Koichi et al., esp@cenet database—worldwide.
Abstract of JP 2007099729, Method for producing alpha-methylstyrene or cumene, Publication date: Apr. 19, 2007, Inventor: Toshio, esp@cenet database—worldwide.
Abstract of RO 119778, Process for preparing perchloroethylene, Publication date: Mar. 30, 2005, Inventor: Horia et al., esp@cenet database—worldwide.
Abstract of WO 0105737, Method for preparing a carboxylic acid, Publication date: Jan. 25, 2001, Inventor: Pascal et al., esp@cenet database—worldwide.
Abstract of WO 0105738, Method for Preparing a carboxylic acid, Publication date: Jan. 25, 2001, Inventor: Pascal et al., esp@cenet database—worldwide.
Abstract of WO 9721656, Method for making fluoroalkanols, Publication date: Jun. 19, 1997, Inventor: Gillet, esp@cenet database—worldwide.
Abstract of WO 9950213, Method for producing dialkyl ethers, Publication date: Oct. 7, 1999, Inventor: Falkowski et al., esp@cenet database—worldwide.
Abstract of WO 2004092099, Method for producing cyclic enols, Publication date: Oct. 28, 2004, Inventor: Friedrich Marko et al., esp@cenet database—worldwide.
Abstract of WO 2006063852, Electroluminescent polymers and use thereof, Publication date: Jun. 22, 2006, Inventor: Buesing Arne et al., esp@cenet database—worldwide.
Abstract of WO 2006076942, Method for the production of synthetic fuels from oxygenates, Publication date: Jul. 27, 2006, Inventor: Rothaemel et al., esp@cenet database—worldwide.
Abstract of WO 2006136135, Method for decarboxylating C—C cross-linking of carboxylic acids with carbon electrophiles, Publication date: Dec. 28, 2006, Inventor: Goossen Lukas et al., esp@cenet database—worldwide.
Abstract of WO 2007028761, Method for chlorinating alcohols, Publication date: Mar. 15, 2007, Inventor: Rohde et al., esp@cenet database—worldwide.
Abstract of WO 2007128842, Catalytic transalkylation of dialkyl benzenes, Publication date: Nov. 15, 2007, Inventor: Goncalvesalmeida et al., esp@cenet database—worldwide.
Abstract of WO 2007137566, Method for catalytic conversion of organic oxygenated compounds from biomaterials, Publication date: Dec. 6, 2007, Inventor: Reschetilowski, esp@cenet database—worldwide.
Adachi et al., Synthesis of sialyl lewis X ganglioside analogs containing a variable length spacer between the sugar and lipophilic moieties, J. Carbohydrate Chemistry, vol. 17, No. 4-5, 1998, pp. 595-607, XP009081720.
Akhrem et al., Ionic Bromination of Ethane and other alkanes (cycloalkanes) with bromine catalyzed by the polyhalomethane-2AlBr3 aprotic organic superacids under mild conditions, Tetrahedron Letters, vol. 36, No. 51, 1995, pp. 9365-9368, Pergamon, Great Britain.
Bagno et al., Superacid-catalyzed carbonylation of methane, methyl halides, methyl alcohol, and dimethyl ether to methyl acetate and acetic acid, J. Org. Chem. 1990, 55, pp. 4284-4289, Loker Hydrocarbon Research Institute; University of Southern California.
Bakker et al., An exploratory study of the addition reactions of ethyleneglycol, 2-chloroethanol and 1,3-dichloro-2-propanol to 1-dodecene, J. Am. Oil Chem. Soc., vol. 44, No. 9, 1967, pp. 517-521, XP009081570.
Benizri et al., Study of the liquid-vapor equilibrium in the bromine-hydrobromic acid-water system, Hydrogen Energy Vector, 1980, pp. 101-116.
Bouzide et al., Highly selective silver (I) oxide mediated monoprotection of symmetrical diols, Tetrahedron Letters, Elsevier, vol. 38, No. 34, 1997, pp. 5945-5948, XP004094157.
Bradshaw et al., Production of hydrobromic acid from bromine and methane for hydrogen production, Proceedings of the 2001 DOE Hydrogen Program Review, NREL/CP-570-30535, 2001, pp. 1-8.
Chang et al., The conversion of methanol and other O—compounds to hydrocarbons over zeolite catalysts, Journal of Catalysis 47, 1977, Academic Press, Inc., pp. 249-259.
Claude et al., Monomethyl-branching of long n-alkanes in the range from decane to tetracosane on Pt/H-ZSM-22 bifunctional catalyst, Journal of Catalysis 190, 2000, pp. 39-48.
Combined International Search Report and Written Opinion dated Apr. 17, 2007 for PCT/US2006/013394, Applicant: GRT, Inc. , pp. 1-13.
Fenelonov, et al., Changes in texture and catalytic activity of nanocrystalline MgO during its transformation to MgCl2 in the reaction with 1-chlorobutane, J. Phys. Chem. B 2001, 105, 2001 American Chemical Society, pp. 3937-3941.
Final Report, Abstract, http://chemelab.ucsd.edu/methanol/memos/final.html, May 9, 2004, pp. 1-7.
Gibson, Phase-transfer synthesis of monoalkyl ethers of oligoethylene glycols, J. Org. Chem. 1980, vol. 45, No. 6, pp. 1095-1098, XP002427776.
http://webbook.nist.gov/, Welcome to the NIST chemistry webbook, Sep. 10, 2007, U.S. Secretary of Commerce on Behalf of the United States of America, pp. 1-2.
Ione, et al., Syntheses of hydrocarbons from compounds containing one carbon atom using bifunctional zeolite catalysts, Solid Fuel Chemistry, Khimiya Tverdogo Topliva, 1982, Allerton Press, Inc., vol. 16, No. 6, pp. 29-43.
Jaumain et al., Direct catalytic conversion of chloromethane to higher hydrocarbons over various protonic and cationic zeolite catalysts as studied by in-situ FTIR and catalytic testing, Studies in Surface Science and Catalysis 130, Elsevier Science B.V., 2000, pp. 1607-1612.
JLM Technology Ltd., The Miller GLA Technology for conversation of light hydrocarbons to alcohols, New Science for the Benefit of Humanity, May 31, 2000; pp. 1-10.
Kirk-Othmer, Encyclopedia of Chemical Technology, 4th Edition, vol. 1, A Wiley-Interscience Publication, John Wiley & Sons, 1991, pp. 946-997.
Liu et al., Higher hydrocarbons from methane condensation mediated by HBr, Journal of Molecular Catalysis A: Chemical 273, Elsevier B.V., 2007, pp. 14-20.

(56) References Cited

OTHER PUBLICATIONS

Loiseau et al., Multigram synthesis of well-defined extended bifunctional polyethylene glycol (PEG) chains, J. Org. Chem., vol. 69, No. 3, XO-002345040, 2004, pp. 639-647.
Lorkovic et al., A novel integrated process for the functionalization of methane and ethane: bromine as mediator, Catalysis Today 98, 2004, pp. 317-322.
Lorkovic et al., C1 oxidative coupling via bromine activation and tandem catalytic condensation and neutralization over CaO/zeolite composites II. Product distribution variation and full bromine confinement, Catalysis Today 98, 2004, pp. 589-594.
Lorkovic et al., C1 coupling via bromine activation and tandem catalytic condensation and neutralization over CaO/zeolite composites, Chem. Comm. 2004, pp. 566-567.
Mihai, et al., Application of Bronsted-type LFER in the study of the phospholipase C Mechanism, J. Am. Chem. Soc., vol. 125, No. 11, XP-002427777, 2003, pp. 3236-3242.
Mishakov et al., Nanocrystalline MgO as a dehydrohalogenation catalyst, Journal of Catalysis 206, Elsevier Science, USA, 2002, pp. 40-48.
Mochida, et al., The catalytic dehydrohalogenation of haloethanes on solid acids and bases, Bulletin of the Chemical Society of Japan, vol. 44, Dec. 1971, pp. 3305-3310.
Motupally et al., Recycling chlorine from hydrogen chloride, The Electrochemical Society Interface, Fall 1998, pp. 32-36.
Murray et al., Conversion of methyl halides to hydrocarbons on basic zeolites: a discovery by in situ NMR, J. Am. Chem. Soc., 1993, vol. 115, pp. 4732-4741.
Nishikawa et al., Ultrasonic relaxations in aqueous solutions of alcohols and the balance between hydrophobicity and hydrophilicity of the solutes, J. Phys. Chem., vol. 97, No. 14, XP-002427775, 1993, pp. 3539-3544.
Olah et al., Antimony pentafluoride/graphite catalyzed oxidative carbonylation of methyl halides with carbon monoxide and copper oxides (or copper/oxygen) to methyl acetate, J. Org. Chem. 1990, 55, pp. 4293-4297.
Olah et al., Antimony pentafluoride/graphite catalyzed oxidative conversion of methyl halides with copper oxides (or copper/oxygen) to dimethyl ether, J. Org. Chem. 1990, 55, pp. 4289-4293.
Olah, Electrophilic methane conversion, American Chemical Society, Acc. Chem. Res. 1987, 20, pp. 422-428.
Olah, Hydrocarbons through methane derivatives, Hydrocarbon Chemistry, 1995, pp. 89-90, John Wiley & Sons, Inc.
Olah et al., Hydrocarbons through methane derivatives, Hydrocarbon Chemistry, 2nd Edition, 2003, pp. 123, 149, and 153, John Wiley & Sons, Inc.
Olah et al., Onium Ylide Chemistry. 1. Bifunctional acid-base-catalyzed conversion of heterosubstituted methanes into ethylene and derived hydrocarbons. The Onium Ylide mechanism of the C1—C2 conversion. J. Am. Chem. Soc. 1984, 106, pp. 2143-2149.
Olah et al., Selective monohalogenation of methane over supported acid or platinum metal catalysts and hydrolysis of methyl halides over γ-alumina-supported metal oxide/hydroxide catalysts. A feasible path for the oxidative conversion of methane into methyl alcohol-dimethyl ether, J. Am. Chem. Soc. 1985, 107, pp. 7097-7105.
Prelog et al., 234. Chirale 2, 2'-polyoxaalkano-9,9'-spirobifluorene, Helvetica Chimica ACTA, vol. 62, No. 7, 1979 pp. 2285-2302.
Rakoff et al., Quimica Organica Fundamental, Organic Chemistry, The Macmillan Company, 1966, pp. 58-63 and 76-77.
Richards, et al., Nanocrystalline ultra high surface area magnesium oxide as a selective base catalyst, Scripta Materialia, 44, 2001, pp. 1663-1666, Elsevier Science Ltd.
Shimizu et al., Gas-Phase electrolysis of hydrobromic acid using PTFE-bonded carbon electrode, Int. J. Hydrogen Energy, vol. 13, No. 6, pp. 345-349, 1988.
Smirnov et al., Selective bromination of alkanes and arylalkanes with CBr4, Mendeleev Commun., 2000, pp. 175-176.
Sun et al., Nanocrystal metal oxide—Chlorine adducts: selective catalysts for chlorination of alkanes, J. Am. Chem. Soc., 1999, 121, pp. 5587-5588.
Sun et al., A general integrated process for synthesizing olefin oxides, Chem. Commun., The Royal Society of Chemistry 2004, pp. 2100-2101.
Tamura et al., The reactions of grignard reagents with transition metal halides: Coupling, disproportionation, and exchange with olefins, Bulletin of the Chemical Society of Japan, vol. 44, Nov. 1971, pp. 3063-3073.
Taylor et al., Direct conversion of methane to liquid hydrocarbons through chlorocarbon intermediates, 1988, Elsevier Science Publishers B.V. Amsterdam, Netherlands, pp. 483-489.
Taylor, Conversion of substituted methanes over ZSM-catalysts, 2000, pp. 3633-3638, Studies in Surface Science and Catalysis 130, Elsevier Science B.V.
Taylor, PETC's on-site naural gas conversion efforts, Preprints of the Fuel Division, 208th National Meeting of the American Chemical Society, 39 (4), 1994, pp. 1228-1232.
Thomas et al., Catalytically active centres in porous oxides: design and performance of highly selective new catalysts, Chem. Commun., 2001, pp. 675-687.
Thomas et al., Synthesis and characterization of a catalytically active nickel-silicoaluminophosphate catalyst for the conversion of methanol to ethene, American Chemical Society, 1991, 3, pp. 667-672.
Van Velzen et al., HBr electrolysis in the Ispra mark 13A flue gas desulphurization process: electrolysis in a DEM cell, Journal of Applied Electrochemistry, 20, 1990, pp. 60-68.
Wagner et al., Reactions of VX, GD, and HD with nanosize CaO: autocatalytic dehydrohalogenation of HD, J. Phys. Chem. B 2000, 104, pp. 5118-5123, 2000 American Chemical Society.
Wauters et al., Electrolytic membrane recovery of bromine from waste hydrogen bromide streams, AIChE Journal, Oct. 1998, vol. 44, No. 10, pp. 2144-2148.
Weissermel et al., Industrial Organic Chemistry, 3rd Edition, 1997, pp. 160-162, and 208.
Whitesides et al., Nuclear magnetic resonance spectroscopy. The effect of structure on magnetic nonequivalence due to molecular asymmetry, J. Am. Chem. Soc., vol. 86, No. 13, 1964, pp. 2628-2634, XP002427774.
Yilmaz et al., Bromine mediated partial oxidation of ethane over nanostructured zirconia supported metal oxide/bromide, Microporous and Mesoporous Materials, 79, 2005, Science Direct, Elsevier, pp. 205-214.
Zhou et al., An integrated process for partial oxidation of alkanes, Chem. Commun., 2003, The Royal Society of Chemistry, pp. 2294-2295.
ZSM-5 Catalyst, http://chemelba.ucsd.edu/methanol/memos/ZSM-5.html, Nov. 6, 2003, p. 1.
Abstract of GB 998681(A), Improvements in or relating to the recovery of bromine from bromine-containing materials, Publication date: Jul. 21, 1965, Applicant: Electro Chimie Metal+, espacenet worldwide database.
Abstract of JP 55-073619, Condensation of methyl chloride through dehydrochlorination, Publication date: Jun. 3, 1980, Inventor: Shigeo et al., http://www19.ipdl.inpit.go.jp/PA1/result . . . .
Hannus, Adsorption and transformation of halogenated hydrocarbons over zeolites, Applied Catalysis A: General 189, 1999, XP-002634422, pp. 263-276.
Howe, Zeolite catalysts for dehalogenation processes, Applied Catalysis A: General 271, 2004, XP-002634421, pp. 3-11.
Li et al., Pyrolysis of Halon 1301 over zeolite catalysts, Microporous and Mesoporous Materials 35-36, 2000, XP-002634423, pp. 219-226.
Chretien; Process for the Adjustment of the HHV in the LNG Plants; 23rd World Gas Conference; Amsterdam 2006; Jun. 5-9, 2006; pp. 1-14.
Yang et al.: Maximising the Value of Surplus Ethane and Cost-Effective Design to Handle Rich LNG; publ. date Jun. 1, 2007; pp. 1-13.
Henshuiinkai, Kagaku Daijiten; Kagaku Daijiten 4, Japan, Kyoritsu Publisher, Oct. 15, 1963; pp. 652-654.
Jacobson, C.A.; "Encyclopedia of Chemical Reactions"; vol. 1, 1946, pp. 722.
U.S. Office Communication from U.S. Appl. No. 12/792,335, dated Aug. 17, 2012.

(56) References Cited

OTHER PUBLICATIONS

U.S. Office Communication from U.S. Appl. No. 12/957,036 dated Aug. 16, 2012.
U.S. Office Communication from U.S. Appl. No. 13/157,584 dated May 11, 2012.
U.S. Office Communication from U.S. Appl. No. 13/157,584 dated Aug. 29, 2012.
U.S. Office Communication from U.S. Appl. No. 10/365,346 dated Jun. 12, 2006.
U.S. Office Communication from U.S. Appl. No. 10/826,885 dated Oct. 31, 2005.
U.S. Office Communication from U.S. Appl. No. 10/826,885 dated Apr. 19, 2006.
U.S. Office Communication from U.S. Appl. No. 10/826,885 dated Jul. 27, 2006.
U.S. Office Communication from U.S. Appl. No. 10/826,885 dated Nov. 2, 2006.
U.S. Office Communication from U.S. Appl. No. 10/826,885 dated Jan. 24, 2007.
U.S. Office Communication from U.S. Appl. No. 10/893,418 dated Jun. 14, 2007.
U.S. Office Communication from U.S. Appl. No. 10/893,418 dated Jan. 2, 2008.
U.S. Office Communication from U.S. Appl. No. 11/091,130 dated Oct. 3, 2007.
U.S. Office Communication from U.S. Appl. No. 11/101,886 dated Jan. 24, 2007.
U.S. Office Communication from U.S. Appl. No. 11/254,438 dated Jan. 24, 2007.
U.S. Office Communication from U.S. Appl. No. 11/254,438 dated Nov. 1, 2007.
U.S. Office Communication from U.S. Appl. No. 11/778,479 dated Feb. 22, 2010.
U.S. Office Communication from U.S. Appl. No. 12/112,926 dated Jan. 16, 2009.
U.S. Office Communication from U.S. Appl. No. 12/112,926 dated Sep. 14, 2009.
U.S. Office Communication from U.S. Appl. No. 12/112,926 dated Jan. 7, 2010.
U.S. Office Communication from U.S. Appl. No. 12/112,926 dated Jul. 22, 2010.
U.S. Office Communication from U.S. Appl. No. 12/112,926 dated Jan. 7, 2011.
U.S. Office Communication from U.S. Appl. No. 12/123,924 dated Mar. 19, 2010.
U.S. Office Communication from U.S. Appl. No. 12/123,924 dated Aug. 30, 2010.
U.S. Office Communication from U.S. Appl. No. 12/139,135 dated Nov. 24, 2010.
U.S. Office Communication from U.S. Appl. No. 12/502,024 dated Oct. 26, 2010.
U.S. Office Communication from U.S. Appl. No. 12/715,526 dated Feb. 17, 2011.
U.S. Office Communication from U.S. Appl. No. 12/139,135 dated Apr. 14, 2011.
U.S. Office Communication from U.S. Appl. No. 12/715,526 dated May 24, 2011.
U.S. Office Communication from U.S. Appl. No. 12/502,024 dated May 31, 2011.
U.S. Office Communication from U.S. Appl. No. 12/139,135 dated Oct. 14, 2011.
U.S. Office Communication from U.S. Appl. No. 12/477,307 dated Oct. 7, 2011.
U.S. Office Communication from U.S. Appl. No. 12/477,319 dated Jul. 22, 2011.
U.S. Office Communication from U.S. Appl. No. 12/502,024 dated Sep. 16, 2011.
U.S. Office Communication from U.S. Appl. No. 12/477,307 dated Feb. 27, 2012.
U.S. Office Communication from U.S. Appl. No. 12/715,526 dated Jan. 4, 2012.
U.S. Appl. No. 60/487,364, Jul. 15, 2003, Lorkovic et al.
U.S. Appl. No. 60/559,844, Apr. 6, 2004, Sherman et al.
U.S. Appl. No. 60/765,115, Feb. 3, 2006, Keefer et al.
Lewis, Richard J., Sr. (2007); Hawley's Condensed Chemical Dictionary (15th Edition); John Wiley & Sons; p. 181.
U.S. Office Communication from U.S. Appl. No. 13/705,106 dated Feb. 3, 2014.
U.S. Office Communication from U.S. Appl. No. 13/713,926 dated Jan. 30, 2014.
U.S. Office Communication from U.S. Appl. No. 13/760,291 dated Apr. 4, 2014.
U.S. Office Communication from U.S. Appl. No. 13/679,600 dated Jan. 17, 2014.
Abstract of JP publication No. 08-283182, Production of Hydrochloromethanes, Publication date: Oct. 29, 1996, Inventor: Kojiro et al., http://www19.ipdl.inpit.go.jp . . . .
Abstract of WO 96/00696, Method and Apparatus for Recovering Bromine from a Liquid Effluent, Publication date: Jan. 11, 1996, Inventor: Mulet, Jean-Charles et al.
Jackisch; "Bromine" in Kirk-Othmer Encyclopedia of Chemical Technology, Fourth Edition, vol. 4, pp. 536-537, 548-550, 560, published 1992, John Wiley & Sons, Inc. USA.
Kesner, Miri; "How is Bromine Produced" in Bromine Compounds from the Dead Sea, Israel Products in the Service of People; pp. 3, 5, 78, 87; First published in Hebrew in Israel in 1999 by the Department of Science Teaching, The Weizmann Institute of Science.
Mills, "Bromine", Ullmann's Encyclopedia of Industrial Chemistry, Fifth, Completely Revised Edition, vol. A4, pp. 391 and 397, published 1985, VCH Verlagsgesellschaft mbH, Federal Republic of Germany.
U.S. Office Communication from U.S. Appl. No. 12/139,135 dated Nov. 7, 2013.
U.S. Office Communication from U.S. Appl. No. 12/792,335 dated Jan. 2, 2013.
U.S. Office Communication from U.S. Appl. No. 13/053,540 dated Aug. 6, 2013.
U.S. Office Communication from U.S. Appl. No. 13/053,540 dated Jan. 8, 2014.
U.S. Office Communication from U.S. Appl. No. 13/117,785 dated Mar. 14, 2013.
U.S. Office Communication from U.S. Appl. No. 13/117,785 dated Apr. 22, 2013.
U.S. Office Communication from U.S. Appl. No. 13/212,291 dated May 10, 2013.
U.S. Office Communication from U.S. Appl. No. 13/269,683 dated Jun. 6, 2013.
U.S. Office Communication from U.S. Appl. No. 13/647,002 dated Jun. 5, 2013.

\* cited by examiner

PROCESSES AND SYSTEMS FOR FRACTIONATION OF BROMINATED HYDROCARBONS IN THE CONVERSION OF NATURAL GAS TO LIQUID HYDROCARBONS

BACKGROUND

The present invention relates generally to processes and systems for converting lower molecular weight alkanes to higher molecular weight hydrocarbons and, more particularly, in one or more embodiments, to processes for converting lower molecular weight alkanes that include fractionation of brominated hydrocarbons, wherein the brominated hydrocarbons are framed by reaction of the lower molecular weight alkanes with bromine.

Natural gas, which is primarily composed of methane and other light alkanes, has been discovered in large quantities throughout the world. In the United States, the latest proved natural gas reserves are 6,731 billion standard cubic meter (238 trillion standard cubic feet) in 2010, which makes the United States a top-five country in natural gas abundance. Natural gas is generally a cleaner energy source than crude oil. It is normally heavy sulfur-free and contains none or a minimum amount of heavy metals and non-reacting heavy hydrocarbons. For a given amount of heat energy, burning natural gas produces about half as much carbon dioxide as coal.

However, the transportation, storage and distribution of natural gas in a gaseous form are much less favorable than those of crude oil making it more difficult to be a substitute as the predominant energy source. Converting natural gas to higher molecular weight hydrocarbons, which, due to their higher density and value, are able to be more economically transported, can significantly aid the development of natural gas reserves, particularly the stranded remote natural gas reserves.

One technique for converting natural gas to higher molecular weight hydrocarbons is a bromine-based process. In general, the bromine-based process may include several basic steps, as listed below.

(1) Bromination: Reacting bromine with lower molecular weight alkanes to produce alkyl bromides and hydrogen bromide (HBr).
(2) Alkyl Bromides Conversion: Reacting the alkyl bromides over a suitable catalyst under sufficient conditions to produce HBr, methane (C1), light end hydrocarbons (C2-C4) and heavy end hydrocarbons (C5+).
(3) HBr Recovery: Recovering HBr produced in both steps (1) and (2) by one of several processes, e.g., absorbing HBr and neutralizing the resulting hydrobromic acid with an aqueous solution of partially oxidized metal bromide salts (as metal oxides/oxy-bromides/bromides) to produce metal bromide salt and water in an aqueous solution; reacting HBr with metal oxide; or absorbing HBr into water using a packed tower or other contacting device.
(4) Bromine Regeneration: Reacting the bromide recovered in step (3) with oxygen or air to yield bromine and treating it sufficiently for recycle to step (1).
(5) Product Recovery: Fractionating by distillation and cryogenic distillation (demethanizer) the hydrocarbon mixtures contained in the effluent from step (2) and then separated from HBr in step (3) into methane, light end hydrocarbons, and heavy end hydrocarbons. The methane can be compressed for recycle to step (1). The light end hydrocarbons (C2-C4) may be, for example, salable as a product or cracked to produce light olefins. The heavy end hydrocarbons (C5+) may be used, for example, for further petrochemical or fuel processing.

In the bromine-based processes, monobrominated alkanes created during bromination may be desirable as the predominant reactant species for the subsequent alkyl bromide conversion. Polybrominated alkanes are known to adversely affect the selectivity profiles of the higher molecular weight hydrocarbons produced during the alkyl bromide conversion and, more importantly, promote the formation of coke which can deposit on the catalyst, block the active sites, and cause rapid catalyst deactivation. The higher selectivity of polybrominated alkanes can also lower the utilization efficiency of bromine, requiring a higher circulating flow of bromine which can correspond to a higher cost in recovering HBr and regenerating recyclable bromine.

To achieve higher selectivity of monobrominated alkanes and reduce the formation of bromination carbon/soot, a large excess of methane or large methane-to-bromine ratio can be used. In the case of the bromination of methane, a methane-to-bromine ratio of about 6:1 can be used to increase the selectivity to mono-bromomethane ($CH_3Br$) to average approximately 88% depending on other reaction conditions. If a lower methane-to-bromine ratio of approximately 2.6:1 is utilized, selectivity of $CH_3Br$ may fall to the range of approximately 65-75% depending, for example, on other reaction conditions. If a methane-to-bromine ratio significantly less than 2.5:1 is utilized, unacceptably low selectivity to $CH_3Br$ occurs, and, moreover, significant formation of undesirable di-bromomethane ($CH_2Br_2$), tri-bromomethane ($CHBr_3$), and carbon soot is observed. However, the large methane-to-bromine ratio can be problematic, in that the large excess methane represents a large recycle stream circulating throughout the entire system. For example, the pressure drop of the process gas between the feed to bromination in step (1) and the recycle methane from product recovery in the step (5) can be large, resulting in a high cost of compression for the recycle gas.

In alkyl bromide conversion, the exothermic coupling reaction may be carried out in a fixed-bed, fluidized-bed or other suitable reactor in the presence of suitable catalysts under sufficient conditions (e.g., 150-600° C., 1-80 bars). The catalyst may have to undergo decoking periodically or continuously to maintain adequate performance. In some instances, a fluidized-bed reactor may be considered to be advantageous for the coupling reaction, particularly for commercial scale of operation, as it should allow for continuous removal of coke and regeneration of the spent catalyst without requiring daily shutdowns and expensive cyclic operation. The fluidized-bed configuration should also facilitate removal of reaction heat and provide a steady selectivity to product composition. However, the fluidized-bed reactor for this particular application may be a very costly item to design and construct as it may have to deal with a high density gas due to the large amount of higher molecular weight bromides contained in the reactor feed (in the forms of HBr and alkyl bromides). Elevated operating pressure, 20-50 bars, may be required to minimize the recompression cost of recycle methane, which, however, will further increase the density of the gases in the synthesis reactor, resulting in a large diameter reactor with heavy wall thickness. In some instances, the catalyst deactivation rate can be lowered by feeding none or the minimum amount of polybromides to the coupling reactor and, thus, the fixed bed configuration may be preferentially selected over fluidized bed.

In product recovery, fresh feed gas may be required to replace the lower molecular weight alkanes converted to products. The fresh feed gas stream containing, for example, primarily methane may necessitate sufficient treating to remove excessive amounts of ethane and higher hydrocarbons prior to being combined with bromine and reacted in a bromination reactor. The feed gas stream may or may not mix with the hydrocarbon mixture exiting HBr recovery prior to receiving such treating. While some ethane and higher hydrocarbons may be tolerated in the bromination reactor, due to the much higher bromination rate of the higher hydrocarbons than that of methane, higher concentrations of the higher hydrocarbon impurities may easily over-brominate and, thus, may result in the rapid formation of carbon-containing coke-like solids, which can cause yield loss and reduced process reliability by fouling and plugging the reactor as well as the downstream units. However, the removal of ethane and higher hydrocarbons from the methane by such means as adsorption or cryogenic distillation can be costly. The cost is higher when both the recycle methane and the fresh feed gas stream require the removal of ethane and higher hydrocarbons. The cost is even higher when high methane-to-bromine ratios are used in the bromination, leading to a large flow rate of recycle methane.

Thus, although progress has been made in the conversion of lower molecular weight alkanes to higher molecular weight hydrocarbons, there remains a need for processes that are more efficient, economic, and safe to operate.

SUMMARY

To achieve the foregoing and other objects, and in accordance with the purposes of the present invention, as embodied and broadly described herein, one embodiment of the present invention is a process that comprises reacting at least gaseous alkanes and a halogen to produce at least a halogenation product stream, wherein the halogenation product stream comprises alkyl halides, hydrogen halide, and unreacted alkanes. The process further may comprise separating the halogenation product stream into at least a gaseous stream and a liquid alkyl halides stream, wherein the gaseous stream comprises hydrogen halide and unreacted alkanes, and wherein the liquid alkyl halides stream comprises alkyl halides. The process further may comprise separating the liquid alkyl halides stream into at least a monohalides stream and a polyhalides stream, wherein the monohalides stream comprises monohalogenated alkanes, and wherein the polyhalides stream comprises polyhalogenated alkanes. The process further may comprise reacting at least a portion of the monohalogenated alkanes from the monohalides stream in the presence of a catalyst to produce at least a synthesis product stream, wherein the synthesis product stream comprises higher molecular weight hydrocarbons and hydrogen halide.

Another embodiment of the present invention is a process that comprises reacting at least gaseous alkanes and bromine in a bromination reactor to produce at least a bromination product stream, wherein the bromination product stream comprise alkyl bromides, hydrogen bromide, and unreacted alkanes. The process further may comprise separating the bromination product stream into at least a gaseous alkane/HBr stream and a liquid alkyl bromides stream, wherein the gaseous alkane/HBr stream comprises hydrogen bromide and unreacted alkanes, and wherein the liquid alkyl bromides stream comprises alkyl bromides. The process further may comprise separating the liquid alkyl bromides stream into at least a monobromides stream and a polybromides stream, wherein the monobromides stream comprises monobrominated alkanes, and wherein the polybromides stream comprises polybrominated alkanes. The process further may comprise reacting at least a portion of the monobrominated alkanes from the monobromides stream in a synthesis reactor to produce at least a synthesis product stream, wherein the synthesis product stream comprises higher molecular weight hydrocarbons and hydrogen bromide. The process further may comprise recovering at least a portion of the hydrogen bromide from the synthesis product stream in a hydrogen bromide separator. The process further may comprise providing a natural gas stream. The process further may comprise separating at least the synthesis product stream and the natural gas stream into at least a light ends product stream, a heavy ends product stream, and a feed gas stream, wherein the light ends product stream comprises light end hydrocarbons having from 2 carbons to 4 carbons, wherein the heavy ends product stream comprises heavy end hydrocarbons having 5 or more carbons, and wherein the feed gas stream comprises methane. The process further may comprise compressing the feed gas stream in a feed compressor. The process further may comprise feeding the feed gas stream into the bromination reactor. The process further may comprise generating a recycle alkane stream by recovering at least a portion of the hydrogen bromide from the gaseous alkane/HBr stream in a second hydrogen bromide separator operating at a higher pressure than the hydrogen bromide separator. The process further may comprise compressing the recycle alkane stream in a recycle compressor. The process further may comprise feeding the recycle alkane stream to the bromination reactor.

Yet another embodiment of the present invention is system that comprises a bromination reactor for reacting at least gaseous alkanes and bromine to produce at least a bromination product stream, wherein the bromination product stream comprises alkyl bromides, hydrogen bromide, and unreacted alkanes. The system further may comprise an alkyl bromides fractionation unit in fluid communication with the bromination reactor for separating the bromination product stream into at least a gaseous alkane/HBr stream and a liquid alkyl bromides stream, wherein the gaseous alkane/HBr stream comprises hydrogen bromide and unreacted alkanes, and wherein the liquid alkyl bromides stream comprises alkyl bromides. The system further may comprise a polybromides fractionation unit in fluid communication with the alkyl bromides fractionation unit for separating the liquid alkyl bromides stream into at least a polybromides stream and a monobromides stream, wherein the polybromides stream comprises polybrominated alkanes, and wherein the monobromides stream comprises monohalogenated bromides. The system further may comprise a synthesis reactor in fluid communication with the polybromides fractionation unit for reacting at least a portion of the monobrominated alkanes from the monobromides stream in the presence of a catalyst to produce a synthesis product stream, wherein the synthesis product stream comprises higher molecular weight hydrocarbons and hydrogen bromide. The system further may comprise a hydrogen bromide separator in fluid communication with the synthesis reactor for recovering at least a portion of the hydrogen bromide from the synthesis product stream. The system further may comprise a second hydrogen bromide separator unit in fluid communication with the alkyl bromides fractionation unit for recovering at least a portion of the hydrogen bromide from the gaseous alkane/HBr stream.

BRIEF DESCRIPTION OF THE DRAWINGS

These drawings illustrate certain aspects of some of the embodiments of the present invention and should not be used to limit or define the invention.

DETAILED DESCRIPTION OF SPECIFIC EMBODIMENTS

Figure 1:
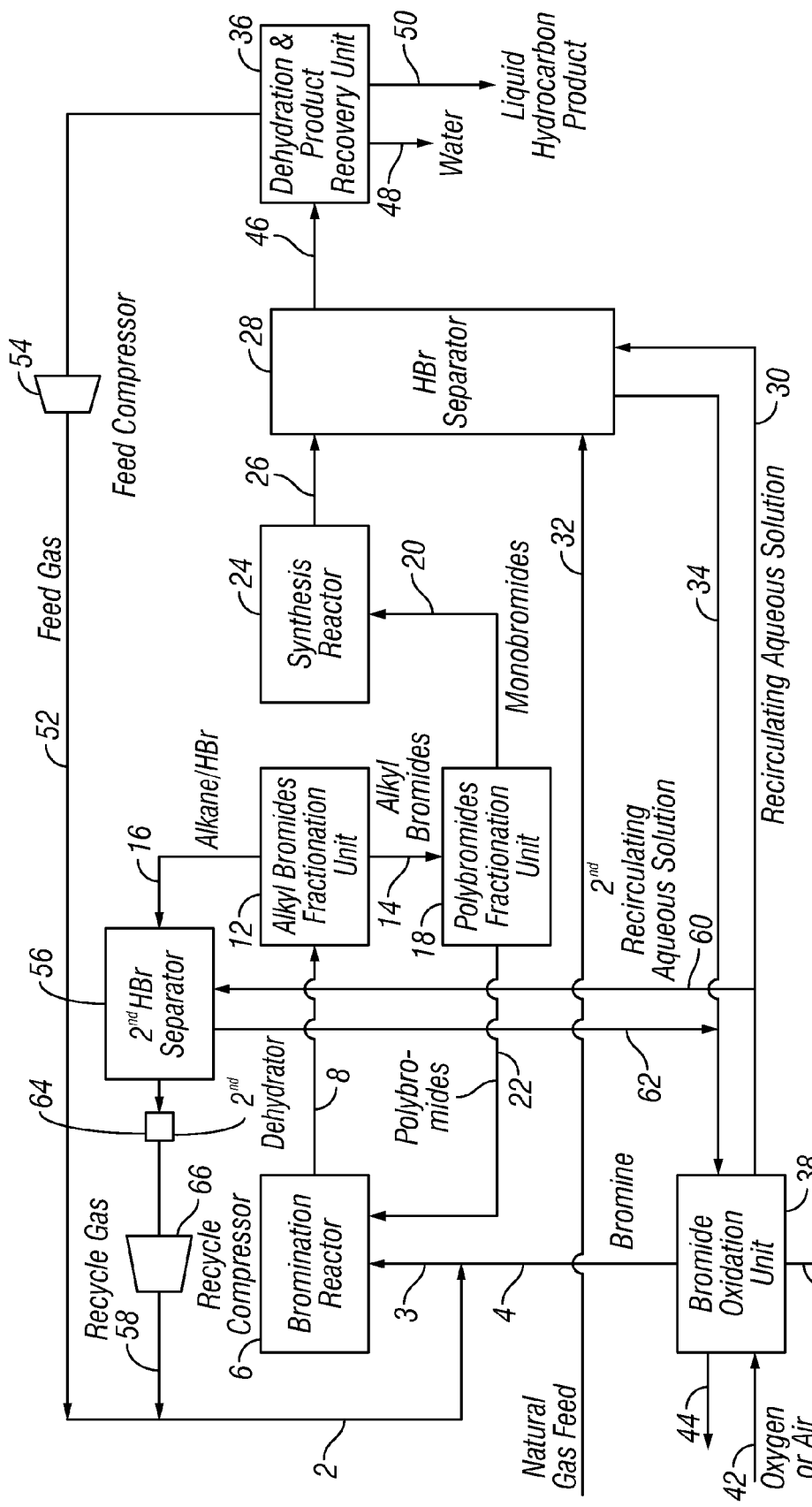
FIG. 1 is a schematic view of a process for the conversion of lower molecular weight alkanes to higher molecular weight hydrocarbons that includes fractionation of brominated hydrocarbons in accordance with embodiments of the present invention.

Embodiments of the present invention are directed to processes for converting lower molecular weight alkanes to higher molecular weight hydrocarbons that include fractionation of brominated hydrocarbons, wherein the brominated hydrocarbons are formed by reaction of the lower molecular weight alkanes with bromine.

There may be many potential advantages to the methods and systems of the present invention, only some of which are alluded to herein. One of the many potential advantages of the embodiments of the systems and methods of the present invention is that separation of the methane from the brominated hydrocarbons should reduce the large recycle stream circulating through the entire process due to the large excess methane that may be used in the bromination step. Accordingly, the bromination step may be performed with a large methane-to-bromine ratio with reasonable recompression cost for recycled methane as embodiments, in accordance with present embodiments. In addition, reduction of the large recycle stream circulating throughout the entire system should also reduce the cost for C2+ alkane separation as the recycle stream should not need to be treated for C2+ alkane removal while still meeting the C2+ alkane specification for feed to the bromination step, in some embodiments. Yet another potential advantage of embodiments of the systems and methods of the present invention is that separation of the methane from the brominated hydrocarbons should reduce the feed rate to the synthesis reactor in the alkyl bromide conversation step. Accordingly, the size of the synthesis reactor can be reduced, which may result in considerable costs savings, especially if a fluidized bed reactor is employed, in accordance with present embodiments. Yet another potential advantage of embodiments of the systems and methods of the present invention is that separation of polybrominated alkanes from the monobrominated alkanes prior to feeding the synthesis reactor should reduce coke formation. Accordingly, the deactivation rate of the catalyst can be slowed, potentially allowing for use of a fixed-bed reactor for commercial-scale production, in certain embodiments.

The term "higher molecular weight hydrocarbons" as used herein refers to hydrocarbons comprising a greater number of carbon atoms than one or more components of the feedstock. For example, natural gas is typically a mixture of light hydrocarbons, predominately methane, with lesser amounts of ethane, propane, and butane, and even smaller amounts of longer chain hydrocarbons such as pentane, hexane, etc. When natural gas is used as a feedstock, higher molecular weight hydrocarbons produced in accordance with embodiments of the present invention may include a hydrocarbon comprising C2 and longer hydrocarbon chains, such as propane, butane, C5+ hydrocarbons, aromatic hydrocarbons, and mixtures thereof. In some embodiments, part or all of the higher molecular weight hydrocarbons may be used directly as a product (e.g., LPG, motor fuel, etc.). In other instances, part or all of the higher molecular weight hydrocarbons may be used as an intermediate product or as a feedstock for further processing. In yet other instances, part or all of the higher molecular weight hydrocarbons may be further processed, for example, to produce gasoline grade fuels, diesel grade fuels, and fuel additives. In some embodiments, part or all of the higher molecular weight hydrocarbons obtained by the processes of the present invention can be used directly as a motor gasoline fuel having a substantial aromatic content, as a fuel blending stock, or as feedstock for further processing such as an aromatic feed to a process producing aromatic polymers, such as polystyrene or related polymers.

The end use of the higher molecular weight hydrocarbons may depend on the particular catalyst employed in the oligomerization portion of the methods discussed below, as well as the operating parameters employed in the process. Other uses will be evident to those skilled in the art with the benefit of this disclosure.

The term "alkyl bromides," as used herein, refers to mono-, di-, and tri-brominated alkanes, and combinations of these. Polybrominated alkanes include di-brominated alkanes, tri-brominated alkanes and mixtures thereof. These alkyl bromides may then be reacted over suitable catalysts so as to form higher molecular weight hydrocarbons.

Lower molecular weight alkanes may be used as a feedstock for the methods described herein. A suitable source of lower molecular weight alkanes may be natural gas. As used herein, the term "lower molecular weight alkanes" refers to methane, ethane, propane, butane, pentane or mixtures of two or more of these individual alkanes. The lower molecular weight alkanes may be from any suitable source, for example, any source of gas that provides lower molecular weight alkanes, whether naturally occurring or synthetically produced. Examples of sources of lower molecular weight alkanes for use in the processes of the present invention include, but are not limited to, natural gas, coal-bed methane, regasified liquefied natural gas, gas derived from gas hydrates and/or clathrates, gas derived from anaerobic decomposition of organic matter or biomass, gas derived in the processing of tar sands, and synthetically produced natural gas or alkanes. Combinations of these may be suitable as well in some embodiments. In some embodiments, it may be desirable to treat the feed gas to remove undesirable compounds, such as sulfur compounds and carbon dioxide. In any event, it is important to note that small amounts of carbon dioxide, e.g., less than about 2 mole %, can be tolerated in the feed gas to the processes of the present invention.

Suitable sources of bromine that may be used in various embodiments of the present invention include, but are not limited to, elemental bromine, bromine salts, aqueous hydrobromic acid, metal bromide salts, and the like. Combinations may be suitable, but as recognized by those skilled in the art, using multiple sources may present additional complications.

FIG. 1 is a schematic diagram illustrating a bromine-based process for the conversion of lower molecular weight alkanes to higher molecular weight hydrocarbons that includes fractionation of alkyl bromides in accordance with one embodiment of the present invention. As illustrated, embodiments of the process may include a bromination reactor 6 for brominating lower molecular alkanes, an alkyl bromides fractionation unit 12 for separation of unreacted alkanes and HBr from the brominated alkanes, a polybromides fractionation unit 18 for separation of polybrominated alkanes from monobrominated alkanes, and a synthesis reactor 24 for production of higher molecular weight hydrocarbons from the monobrominated alkanes. In the illustrated embodiment, the process further includes an HBr separator 28 for recovery of HBr from the higher molecular weight hydrocarbons, a dehydration and product recovery unit 36, and a bromide oxidation unit 38 for recovery of elemental bromine. The process may also include a second HBr separator 56 for recovery of HBr from the unreacted alkanes, a second dehydrator 64 for dehydration of the unreacted alkanes to form a recycle gas stream 58, and a recycle compressor 66 for compressing the recycle gas stream 58.

In the illustrated embodiment, a gas stream 2 comprising lower molecular weight alkanes (which, in some embodiments, may include a mixture of feed gas stream 52 plus recycled gas stream 58) and a bromine stream 4 may be combined and introduced into a bromination reactor 6. In the illustrated embodiment, the gas stream 2 and the bromine stream 4 are premixed to form a bromination feed gas stream 3 prior to feeding the bromination reactor 6. In an alternative embodiment (not illustrated), the gas stream 2 and bromine stream 4 may be combined in the bromination reactor 6. The gas stream 2 and bromine stream 4 may be allowed to react in the bromination reactor 6 to form a bromination product stream 8 that comprises alkyl bromides, HBr vapor, and unreacted alkanes. The bromination product stream 8 may be withdrawn from the bromination reactor 6.

In the bromination reactor 6, the lower molecular weight alkanes in the gas stream 2 may be reacted exothermically with the bromine in the bromine stream 4, for example, at a temperature in the range of about 250° C. to about 600° C., and at a pressure in the range of about 1 bar to about 50 bars to produce gaseous alkyl bromides and HBr. In an embodiment, the operating pressure of the bromination reactor 6 may range from about 20 bars to about 40 bars, for example, to minimize recompression costs and to maximize the condenser temperature required for the alkyl bromides fractionation step. In some embodiments, the feeds to the bromination reactor 6 may be pre-heated to a temperature of about 250° C. to about 400° C., for example, in an inlet pre-heater zone. It should be understood that the upper limit of the operating temperature range is greater than the upper limit of the reaction initiation temperature range to which the feed mixture may be heated due to the exothermic nature of the bromination reaction. Those of ordinary skill in the art will appreciate that the bromination reaction may be a non-catalytic (thermal) or a catalytic reaction as will be appreciated by those of ordinary skill in the art. Bromination of alkanes is described in more detail in U.S. Pat. No. 7,674,941, the disclosure of which is incorporated herein by reference. In the case of methane, it is believed that the formation of multiple brominated compounds occurs in accordance with the following general overall reaction:

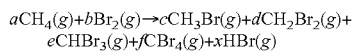

The methane/bromine molar ratio of the feed introduced to the bromination reactor 6 may be at least about 2.5:1, in some embodiments. In alternative embodiments, a larger excess of methane (e.g., about 3:1 to about 10:1) may be used in order to achieve desirable selectivity of $CH_3Br$ and reduce the formation of soot, $CH_3Br$ is more rapidly brominated than methane under free radical conditions. The C2+ alkanes entering the bromination reactor 6 are known to more rapidly form polybrominated alkanes and coke/soot, as they are much more easily brominated than methane. Accordingly, in some embodiments, the C2+ alkane content entering the bromination reactor 6 can be controlled by treating the natural gas feed stream 32 or its mixture with the hydrocarbon products formed in the synthesis reactor 24 using any suitable means, such as cryogenic separation. In some embodiment, the C2+ alkane concentration in the total alkanes fed to the bromination reactor 6 is less than about 10 mole % in one embodiment, less than about 1 mole % in another embodiment, less than about 0.2 mole % in another embodiment, and less than about 0.1 mole % in yet another embodiment.

As illustrated, the bromination product stream 8 comprising alkyl bromides, HBr vapor, and unreacted alkanes can be withdrawn from the bromination reactor 6 and fed to an alkyl bromides fractionation unit 12. In the alkyl bromides fractionation unit 12, the bromination product stream 8 may be separated into a liquid alkyl bromides stream 14 and a gaseous alkane/HBr stream 16. The liquid alkyl bromides stream 14 may comprise monobrominated alkanes (e.g., $CH_3Br$ and other heavier monobrominated alkanes) and polybrominated alkanes (e.g., $CH_2Br_2$ and other heavier polybrominated alkanes), and the gaseous alkane/HBr stream 16 may comprise unreacted alkanes and HBr.

In some embodiments, the liquid alkyl bromides stream 14 may be fed to the polybromides fractionation unit 18. Prior to entering the polybromides fractionation unit 18, the liquid alkyl bromides stream 14 may be pumped to a higher pressure or let down to a lower pressure, as desired for a particular application. In some embodiments, the polybromides bromides fractionation unit 18 may have an operating pressure from about 1 bar to about 20 bars, for example, to minimize reboiler temperature (e.g., <250° C., alternatively, <200° C.) required for the polybromides fractionation while allowing the use of an inexpensive cooling medium (e.g., cooling water or air cooler) for the overhead condenser. In the polybromides fractionation unit 18, the liquid alkyl bromides stream 14 may be separated into a monobromides stream 20 comprising $CH_3Br$ and other heavier monobrominated alkanes and a polybromides stream 22 comprising $CH_2Br_2$ and other heavier polybrominated alkanes. In the illustrated embodiment, the polybromides stream 22 is returned to the bromination reactor 6 for reproportionating with lower molecular weight alkanes to produce a quantity of monobrominated alkanes in addition to those produced from reaction of the bromine and lower molecular alkanes. While not illustrated by FIG. 1, reproportionation of the polybrominated alkanes in the polybromides stream 22 may occur in a separate reactor from the bromination reactor 6 in accordance with alternative embodiments.

The monobromides stream 20 comprising $CH_3Br$ and other heavier monobrominated alkanes may be vaporized and fed to the synthesis reactor 24. In the synthesis reactor 24, the monobrominated alkanes may be reacted over a suitable catalyst under sufficient conditions via a catalytic coupling reaction to produce higher molecular weight hydrocarbons and additional HBr vapor. By separating some or all of the polybrominated alkanes from the feed to the synthesis reactor 24, coke formation in the synthesis reactor 24 may be reduced.

By reducing coke formation in the synthesis reactor 24, the deactivation rate of the catalyst may be reduced. Due to this reduction in the deactivation rate, a fixed-bed reactor may be suitable, in some embodiments, even for commercial-scale production. In alternative embodiments, a fluidized-bed reactor may be used. Those of ordinary skill in the art will appreciate, with the benefit of this disclosure, that the particular higher molecular weight hydrocarbons produced will be dependent, for example, upon the catalyst employed, the composition of the alkyl bromides introduced, and the exact operating parameters employed. Catalysts that may be employed in the synthesis reactor 24 include synthetic crystalline alumino-silicate catalysts as will be recognized by those of ordinary skill in the art. Formation of higher molecular weight hydrocarbons from reaction of alkyl bromides is described in more detail in U.S. Pat. No. 7,674,941.

As illustrated, a synthesis product stream 26 comprising the higher molecular weight hydrocarbons may be withdrawn from the synthesis reactor 24 and fed to the HBr separator 28 for recovery of HBr. In some embodiments, the synthesis product stream 26 further may comprise an unintended amount of methane produced in the synthesis reactor 24 and the HBr vapor produced in the synthesis reactor 24. In the HBr separator 28, any of a variety of different suitable techniques may be used for separation of HBr, including, but not limited to, the techniques disclosed in U.S. Pat. No. 7,674,941. Non-limiting examples of techniques for HBr separation include absorption of HBr into an aqueous solution or adsorption of HBr on a metal oxide. In the illustrated embodiment, the synthesis product stream 26 may be contacted with recirculating aqueous solution 30 in the HBr separator 28 to recover HBr from the hydrocarbons by absorbing it into the aqueous solution. The resultant aqueous solution comprising HBr dissolved therein may be removed from the HBr separator 28 via aqueous HBr stream 34.

As illustrated, natural gas feed stream 32 may enter the HBr separator 28 for recovery of hydrocarbons or other purposes. For example, the natural feed gas stream 32 may strip out any residual hydrocarbons in the resultant aqueous solution comprising HBr dissolved therein, depending on the solubility of the hydrocarbons in the aqueous solution at the operating conditions. While not illustrated by FIG. 1, the natural gas feed stream 32 may alternatively be fed directly to the product recovery unit 36 for removal of C2+ hydrocarbons. While the present embodiment describes the use of natural gas feed stream 32, as discussed above, embodiments of the present invention encompass the use of other feedstocks of lower molecular weight alkanes.

The aqueous HBr stream 34 from the HBr separator 28 may then be routed to a bromide oxidation unit 38, in some embodiments, to convert the dissolved HBr to elemental bromine using, for example, air or oxygen and to regenerate the aqueous solution for reuse in the HBr separator 28. The regenerated aqueous solution may then be recirculated to the HBr separator 28 via recirculating aqueous solution 30. The bromine may then be treated sufficiently and sent to the bromination reactor 6 via bromine stream 4. In some embodiments, the bromine that is feed into the bromination reactor 6 may be dry bromine in that the bromine is substantially water-free. Effluent water 40 may also be removed from the bromide oxidation unit 38. Line 42 may be used to supply the oxygen or air fed to the bromide oxidation unit 38. Residual oxygen or spent air may be removed from the oxidation unit via line 44.

Hydrocarbon stream 46 comprising an unintended amount of methane produced in the synthesis reactor 24, higher molecular weight hydrocarbons, and the feed gas may be withdrawn from the HBr separator 28. The hydrocarbon stream 46 may be substantially HBr free, in accordance with embodiments of the present invention, for example, containing less than about 1 mppm HBr and alternatively less than 0.1 mppm HBr. As illustrated, the hydrocarbon stream 46 may be routed to dehydration and product recovery unit 36 wherein water may be removed from the remaining constituents, higher molecular weight hydrocarbons may be recovered as liquid hydrocarbon products, and lower molecular weight hydrocarbons (e.g., methane, ethane, etc.) may be recycled to the bromination reactor 6. Any suitable method of dehydration and product recovery may be used, including, but not limited to, solid-bed desiccant adsorption followed by refrigerated condensation, cryogenic separation, or circulating absorption oil or some other suitable solvent. As illustrated, water may be removed via water stream 48. A liquid hydrocarbon product stream 50 comprising higher molecular weight hydrocarbons may be withdrawn for use as a fuel, a fuel blend, or for further petrochemical or fuel processing, for example.

In the illustrated embodiment, the feed gas stream 52 comprising methane from the dehydration and product recovery unit 36 may be fed to the bromination reactor 6 via the feed compressor 54. As illustrated, the feed gas stream 52 may be combined with recycle gas stream 58 prior to feeding the bromination reactor 6. It should be understood that the feed gas stream 52 may also comprise some C2+ alkanes so long as the C2+ content of the alkanes in gas stream 2 (e.g., feed gas stream 52+recycle gas stream 58) fed to the bromination reactor 6 is less than a predetermined value.

As previously mentioned, the alkyl bromides fractionation unit 12 separates the bromination product stream 8 into a liquid alkyl bromides stream 14 comprising monobrominated alkanes and other heavier alkyl bromides and a gaseous alkane/HBr stream 16 comprising unreacted alkanes and HBr. In the illustrated embodiment, the gaseous alkane/HBr stream 16 may be withdrawn from the alkyl bromides fractionation unit 12 and fed to a second HBr separator 56. By routing the gaseous alkane/HBr stream 16 to the second HBr separator 56, in some embodiments, the unreacted alkanes and HBr separated in the alkyl bromides fractionation unit 12 are not fed to the synthesis reactor 24. Accordingly, in accordance with embodiments, the feed to the synthesis reactor 24 should be reduced, and the size of the synthesis reactor 24 can be reduced, resulting in cost savings.

In the second HBr separator 56, any of a variety of different suitable techniques may be used to produce a recycle gas stream 58 by separation of HBr, including, but not limited to, the techniques disclosed in U.S. Pat. No. 7,674,941. Non-limiting examples of techniques for HBr separation include absorption of HBr into an aqueous solution or adsorption of HBr on a metal oxide. In some embodiments, the HBr can be recovered from the unreacted alkanes by absorbing the HBr into an aqueous solution using, for example, a packed column or other suitable contacting device. In the illustrated embodiment, the gaseous alkane/HBr stream 16 may be contacted with second recirculating aqueous solution 60 in the second HBr separator 56 to recover HBr from the hydrocarbons by absorbing it into the aqueous solution.

The second HBr separator 56 and the HBr separator 28 may use the same or different techniques for the removal of HBr from the hydrocarbon streams (e.g., alkane/HBr stream 16, synthesis product stream 26). In addition, the second HBr separator 56 can operate at a different, and preferably, higher pressure than the HBr separator 28 which recovers HBr from the synthesis product stream 26. For example, the second HBr separator 56 can operate at a pressure that is at least about 3 bars higher than the HBr separator 28. In some embodiments, the second HBr separator 56 may operate at a pressure of about 5 bars to about 50 bars while the HBr separator 28 operates at a pressure of about 2 bars to about 47 bars.

The resultant aqueous solution comprising HBr dissolved therein may be removed from the second HBr separator 56 via second aqueous HBr stream 62, in accordance with embodiments of the present invention. The second aqueous HBr stream 62 may be combined with the aqueous HBr stream 34 from the HBr separator 28 and fed to the bromide oxidation unit 38, described above, to produce elemental bromine and regenerate the aqueous solutions for reuse in the HBr separator 28 and the second HBr separator 56. While FIG. 1 illustrates combination of the aqueous HBr stream 34 and second aqueous HBr stream 62 prior to entering the bromide oxidation unit 38, embodiments (not illustrated) may include separately feeding the aqueous HBr streams 34, 62 to the bromide oxidation unit 38.

As illustrated, the recycle gas stream 58 from the second HBr separator 56 may be fed to the second dehydrator 64 for removal of water and then to a recycle compressor 66 for recompression. After dehydration and recompression, the recycle gas stream 58 may be mixed with the feed gas stream 52 from the dehydration and product recovery unit 36 and routed to the bromination reactor 6 without further cryogenic treatment. Therefore, the process cost to control the presence of C2+ alkanes in the bromination reactor 6 is independent of the molar ratio of methane to bromine. In other words, the use of a large excess of methane should not increase the process cost associated with C2+ alkane control as the unreacted alkanes are not circulated throughout the entire system as disclosed in the process schemes used heretofore. While FIG. 1 illustrates combination of the recycle gas stream 58 and the feed gas stream 52 prior to entering the bromination reactor 6, embodiments (not illustrated) may include separately feeding the recycle gas stream 58 and the feed gas stream 52 to the bromination reactor 6.

In the embodiment illustrated by FIG. 1, the unreacted alkanes separated from the alkyl bromides in the alkyl bromides fractionation unit 12 are only circulating through the bromination reactor 6, the alkyl bromides fractionation unit 12, the second HBr separator 56, and the second dehydrator 64, enduring much less pressure drop by avoiding circulation through the entire system as disclosed in the process schemes used heretofore. As a result, the increase in compression cost for using a large excess of methane or high methane-to-bromine ratio in the bromination reactor 6 can be minimized by incorporation of embodiments of the present invention.

Figure 2:
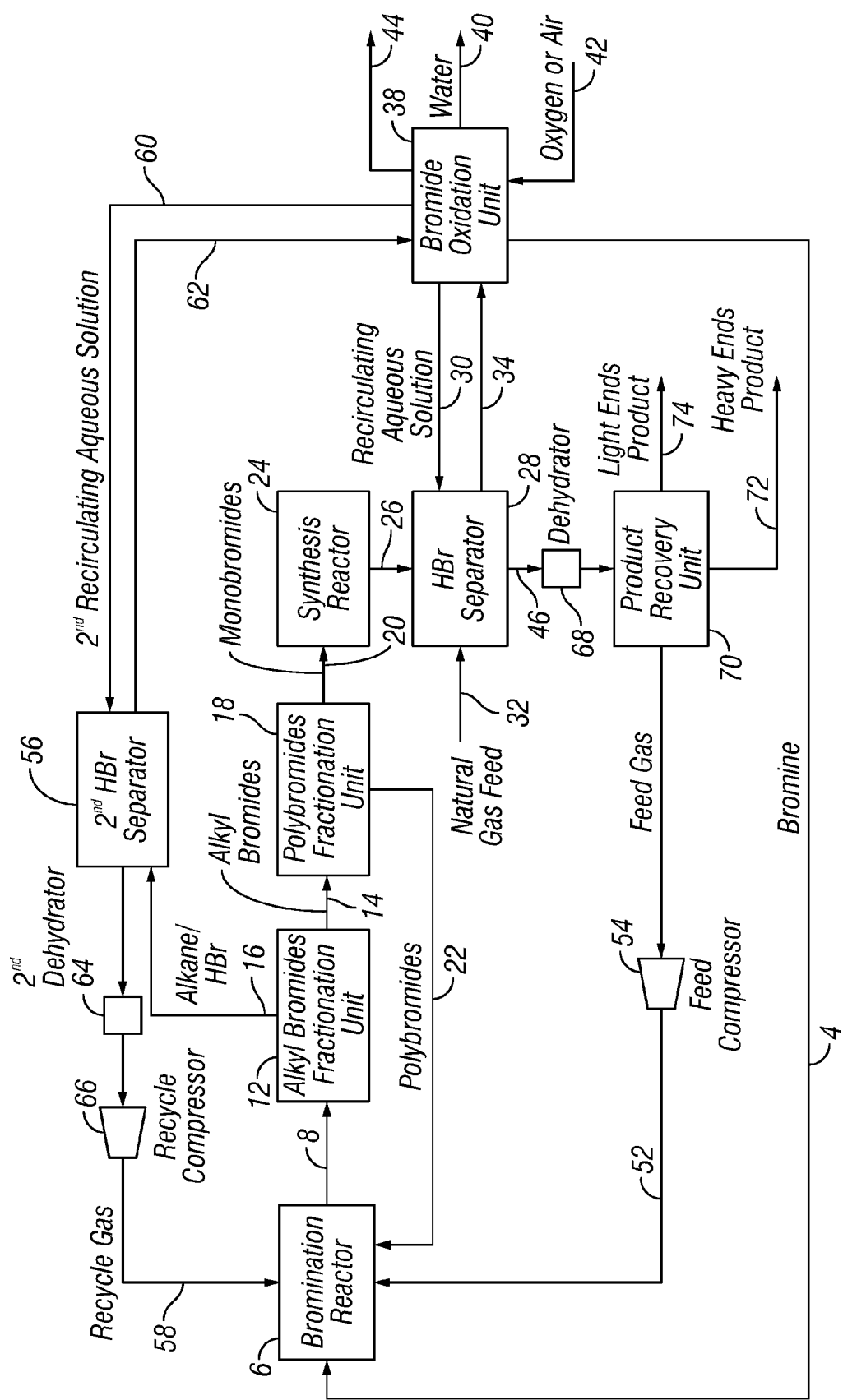
FIG. 2 is a schematic view of another embodiment of a process of the present invention for the conversion of lower molecular weight alkanes to higher molecular weight hydrocarbons that includes fractionation of brominated hydrocarbons, which also produces light end hydrocarbons as another product.

Referring now to FIG. 2, a bromine-based process is illustrated for the conversion of lower molecular weight alkanes to higher molecular weight hydrocarbons that includes fractionation of brominated hydrocarbons in accordance with another embodiment of the present invention. The illustrated embodiment is similar to that illustrated by FIG. 1 except that a light ends product stream 74 comprising C2-C4 hydrocarbons is specified as an additional product from the product recovery unit 70. It should be understood that when the light ends product stream 74 is specified, the feed gas stream 52 routed to the bromination reactor 6 can contain substantially pure methane, in some embodiments, in that the C2+ alkane concentration in the feed gas stream 52 may be less than about 1 mole %, in one embodiment, and less than about 0.1 mole %, in another embodiment.

In the illustrated embodiment, hydrocarbon stream 46 comprising an unintended amount of methane produced in the synthesis reactor 24, higher molecular weight hydrocarbons, and the feed gas may be withdrawn from the HBr separator 28 and routed to a dehydrator 68 for removal of water and then a product recovery unit 70 for recovery of a heavy ends product stream 72 comprising C5+ hydrocarbons, a light ends product stream 74 comprising C2-C4 hydrocarbons, and a feed gas stream 52 comprising methane. Any suitable method of dehydration and product recovery may be used, including, but not limited to, solid-bed desiccant adsorption followed by refrigerated condensation, cryogenic separation, or circulating absorption oil or some other solvent.

The feed gas stream 52 comprising methane from the product recovery unit 70 may be fed to the bromination reactor 6 via the feed compressor 54. It should be understood that the feed gas stream 52 may also comprise some C2+ alkanes so long as the C2+ content of the alkanes (e.g., feed gas stream 52+recycle gas stream 58) fed to the bromination reactor 6 is less than a predetermined value. While FIG. 2 illustrates the feed gas stream 52 and the recycle gas stream 58 as separate streams, it should be understood that embodiments include premixing the feed gas stream 52 and the recycle gas stream 58 prior to feeding the bromination reactor 6.

Figure 3:
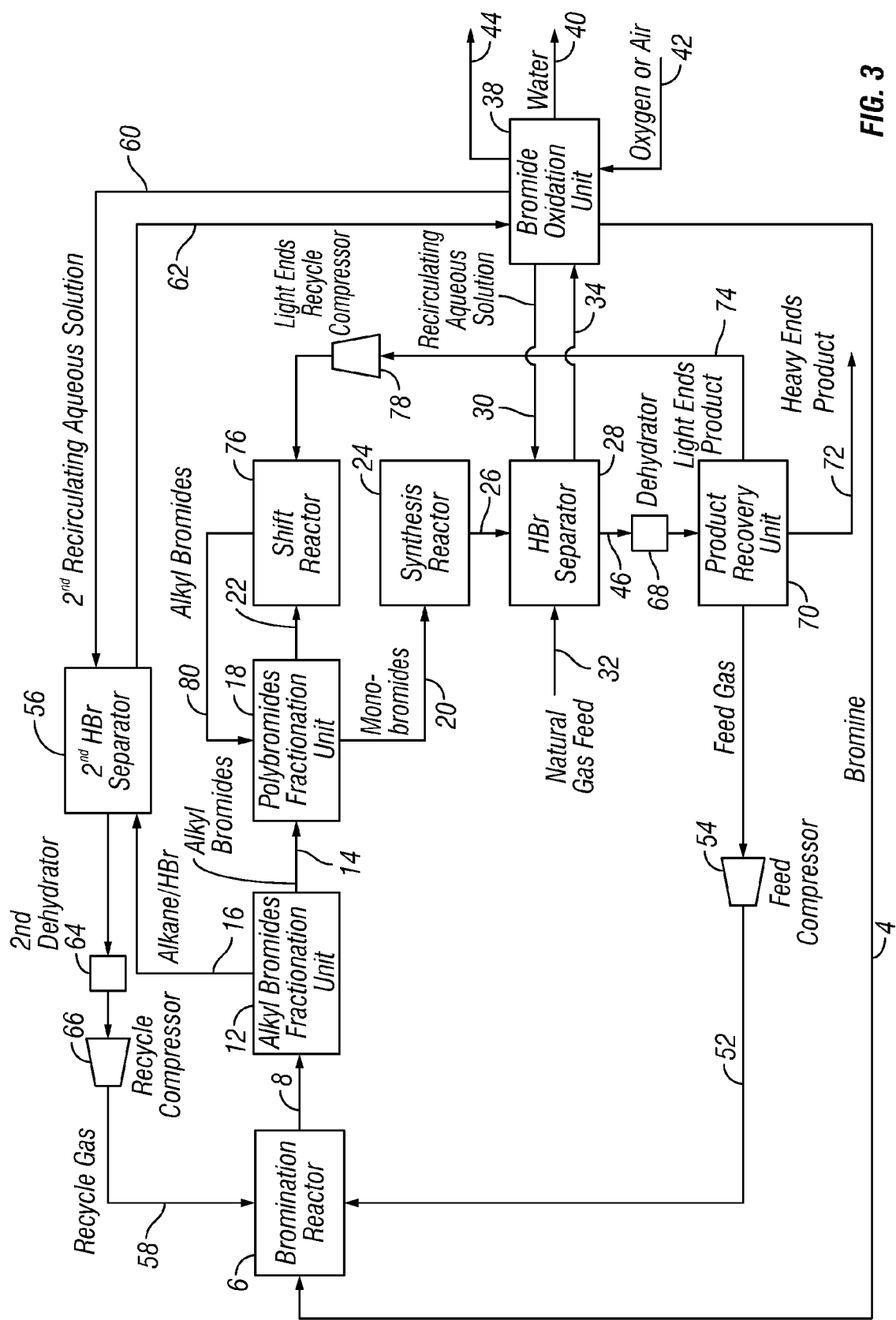
FIG. 3 is a schematic view of another embodiment of a process of the present invention for the conversion of lower molecular weight alkanes to higher molecular weight hydrocarbons that includes fractionation of brominated hydrocarbons configured to incorporate a shift reactor for reducing the content of polybrominated alkanes fed to the synthesis reactor.

Referring now to FIG. 3, a bromine-based process is illustrated for the conversion of lower molecular weight alkanes to higher molecular weight hydrocarbons that includes fractionation of brominated hydrocarbons in accordance with another embodiment of the present invention. The illustrated embodiment is similar to that illustrated in FIG. 2 except that the light ends product stream 74 comprising C2-C4 hydrocarbons is recycled to reproportionate polybrominated alkanes in a shift reactor 76, producing a quantity of monobrominated alkanes in addition to those produced in the bromination reactor 6.

As illustrated, the light ends product stream 74 comprising C2-C4 hydrocarbons may be fed to the shift reactor 76 via a light ends recycle compressor 78. The polybromides stream 22 from the polybromides fractionation unit 18 comprising $CH_2Br_2$ and other heavier polybrominated alkanes may also be fed to the shift reactor 76. In some embodiments, the feeds may be vaporized prior to their introduction into the shift reactor 76. In the shift reactor 76, at least a portion of the polybrominated alkanes in the polybromides stream 22 can be reproportionated into monobrominated alkanes, thus increasing the content of monobrominated alkanes in the feed to the synthesis reactor 24. This shift reaction occurs by reaction of the C2-C4 hydrocarbons in the light ends product stream 74 with the polybrominated alkanes to form monobrominated alkanes, such as $CH_3Br$, ethyl bromide ($C_2H_5Br$), propyl bromide ($C_3H_7Br$), and the like. In some embodiments, the shift reaction may proceed thermally without a catalyst.

In another embodiment, the shift reaction may be a catalytic reaction. Example techniques for reproportionation of polybrominated alkanes via a shift reaction are described in more detail in U.S. Pat. No. 7,674,941.

In the illustrated embodiment, a reproportionated alkyl bromides stream 80 comprising monobrominated alkanes, unreacted C2-C4 hydrocarbons, and unconverted polybromides may be withdrawn from the shift reactor 76 and routed back to the polybromides fractionation unit 18. As previously discussed, the polybromides fractionation unit 18 also receives a liquid alkyl bromides stream 14 as a feed from the alkyl bromides fractionation unit 12. In the illustrated embodiment, the polybromides fractionation unit 18 separates the reproportionated alkyl bromides stream 80 and liquid alkyl bromides stream 14 into a monobromides stream 20 and a polybromides stream 22. In one embodiment, the monobromides stream 20 may be fed to the synthesis reactor 24 for reaction over a suitable catalyst to produce higher molecular weight hydrocarbons. As illustrated, the polybromides stream 22 may be fed to the shift reactor 76 for another round of reproportionation.

Figure 4:
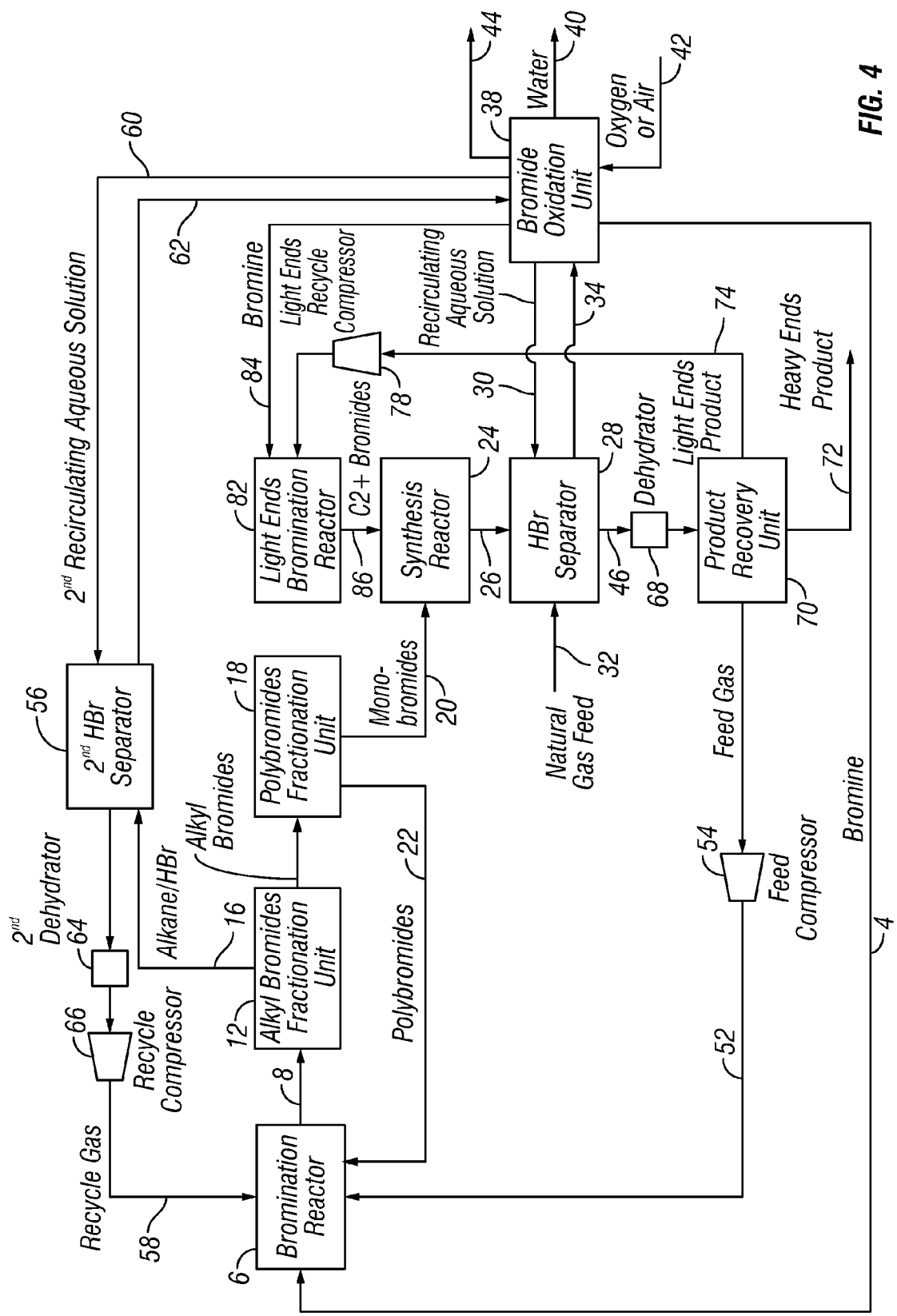
FIG. 4 is a schematic view of another embodiment of a process of the present invention for the conversion of lower molecular weight alkanes to higher molecular weight hydrocarbons that includes fractionation of brominated hydrocarbons with recycle of light end hydrocarbons to produce light end bromides for an additional feed to the synthesis reactor.

Referring now to FIG. 4, a bromine-based process is illustrated for the conversion of lower molecular weight alkanes to higher molecular weight hydrocarbons that includes fractionation of brominated hydrocarbons in accordance with another embodiment of the present invention. The illustrated embodiment is similar to that illustrated in FIG. 2 except that the light ends product stream 74 comprising C2-C4 hydrocarbons is recycled to a light ends bromination reactor 82 to produce C2+ bromides, preferably C2+ monobromides, for additional feed to the synthesis reactor 24.

As illustrated, the light ends product stream 74 may be fed to the light ends bromination reactor 82 via light ends recycle compressor 78. In the light ends bromination reactor 82, the light end hydrocarbons may be allowed to react with bromine fed to the reactor 82 via line 84 to form products that comprise C2+ alkyl bromides, HBr vapor, and unreacted light end hydrocarbons.

In some embodiments, the light ends bromination reactor 82 may operate at milder conditions than the bromination reactor 6. For example, the light ends bromination reactor 82 may operate at a temperature in the range of about 200° C. to about 500° C., alternatively about 235° C. to about 450° C., and alternatively about 250° C. to about 425° C. By way of further example, the light ends bromination reactor 82 may operate at a pressure in the range of about 1 bar to about 80 bars, alternatively about 10 bars to about 50 bars, and alternatively about 20 bars to about 40 bars. In one embodiment, the light ends bromination reactor 82 may operate at a temperature in the range of about 250° C. to about 425° C., and at a pressure in the range of about 15 bars to about 35 bars while the bromination reactor 6 may operate at a temperature in the range of about 350° C. to about 500° C. and a pressure of about 25 bars to about 40 bars.

The effluent that contains the C2+ alkyl bromides, HBr vapor, and unreacted light end hydrocarbons may be withdrawn from the light ends bromination reactor 82 and fed to the synthesis reactor 24 via line 86. In the synthesis reactor 24, the C2+ alkyl bromides may react over a suitable catalyst to produce higher molecular weight hydrocarbons. While the effluent in line 86 from the light ends bromination reactor 82 and the monobromides stream 20 from the alkyl bromides fractionation unit 12 comprising $CH_3Br$ and other heavier monobrominated alkanes are illustrated as separate feeds to the synthesis reactor 24, it should be understood that present embodiments encompass processes in which these streams are combined prior to the synthesis reactor 24.

Figure 5:
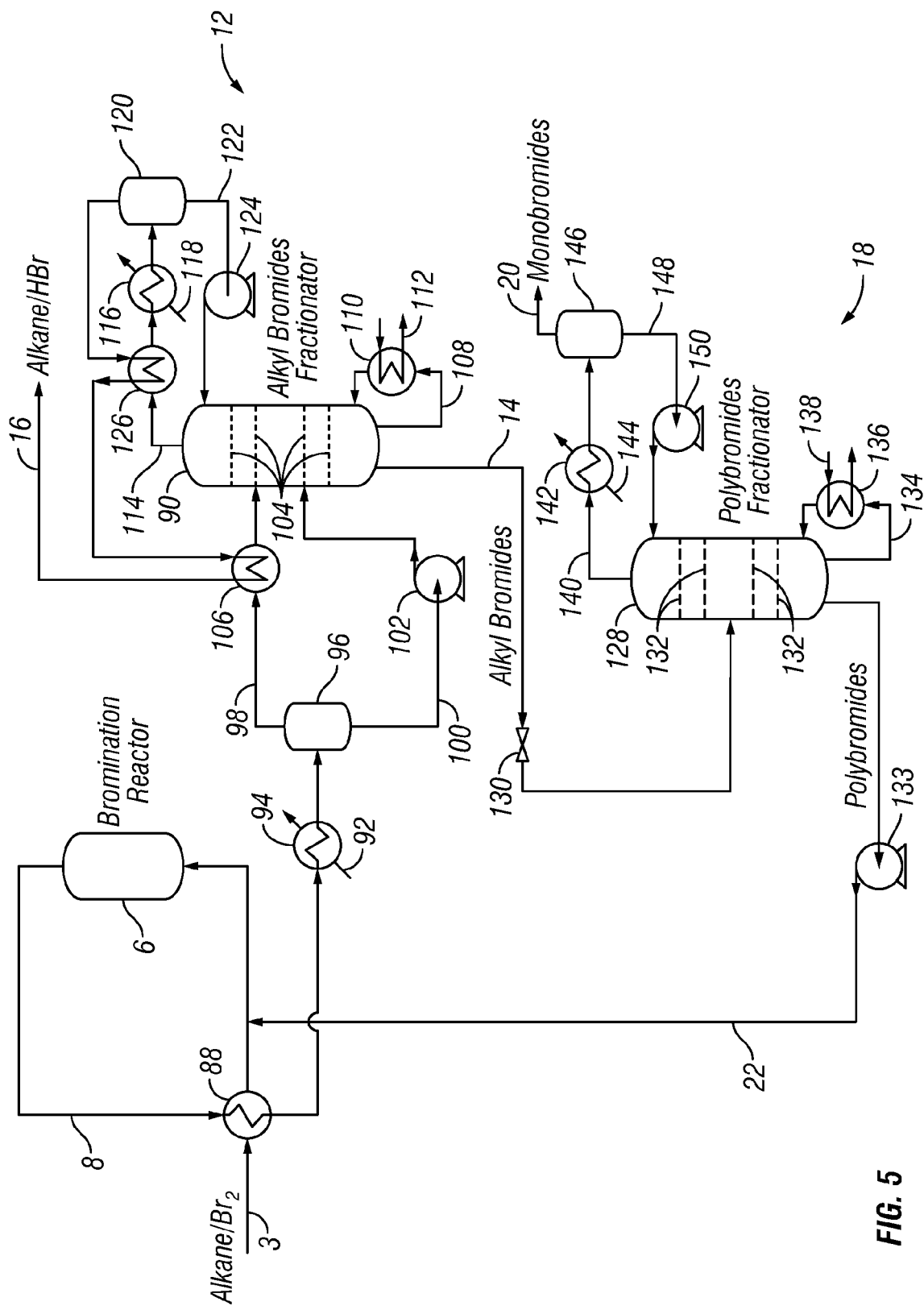
FIG. 5 is a schematic view of alkyl bromides and polybromides fractionation units in accordance with one embodiment of the present invention.

Referring now to FIG. 5, fractionation of brominated hydrocarbons via an alkyl bromides fractionation unit 12 and a polybromides fractionation unit 18 is illustrated in accordance with embodiments of the present invention. In the illustrated embodiment, the alkyl bromides fractionation unit 12 separates the bromination product stream 8 into a gaseous alkane/HBr stream 16 and a liquid alkyl bromides stream 14, and the polybromides fractionation unit 18 separates the liquid alkyl bromides stream 14 into a monobromides stream 20 and a polybromides stream 22.

As illustrated, a bromination feed gas stream 3 comprising lower molecular weight alkanes (which, in some embodiments, may include a mixture of feed gas stream 52 plus the recycled gas stream 58, as shown on FIG. 1) and bromine may be heated against the bromination product stream 8 in a bromination feed/product cross heat exchanger 88. The bromination feed gas stream 3 may be heated to a temperature of about 250° C. to about 450° C., in one embodiment, and about 300° C. to about 400° C. in another embodiment. The heated bromination feed gas stream 3 may then be combined with polybromides stream 22 from the polybromides fractionator 18 and fed to the bromination reactor 6. In some embodiments, the heated bromination feed gas stream 3 vaporizes the polybromides stream 22 prior to entering the bromination reactor 6.

In the bromination reactor 6, the lower molecular weight alkanes from the feed gas stream 3 may react with bromine to produce brominated alkanes and HBr vapor. In addition, at least a portion of the polybrominated alkanes in the polybromides stream 22 can be reproportionated into monobrominated alkanes. This reproportionation occurs by reaction of the lower molecular weight alkanes in the feed gas stream 3 with the polybrominated alkanes to form monobrominated alkanes, such as $CH_3Br$, $C_2H_5Br$, and the like. In one embodiment, the bromination and reproportionation reactions may result in an adiabatic temperature rise to about 450° C. to about 550° C. while producing a bromination product stream 8 comprising gaseous alkyl bromides and HBr. In some embodiments, the bromination reactor 6 may be operated at a pressure in the range of about 1 bar to about 50 bars. To minimize recompression costs and to maximize condenser temperature in the alkyl bromides fractionator 90, the bromination reactor 6 may be operated, for example, at a pressure of about 20 bars to about 40 bars. A bromination product stream 8 comprising the alkyl bromides (e.g., $CH_3Br$ and other brominated alkanes), HBr vapor, and unreacted alkanes may be withdrawn from the bromination reactor 6.

In the illustrated embodiment, the bromination product stream 8 can first be cooled prior to entering the alkyl bromides fractionator 90 for separation of the unreacted methane and HBr from the alkyl bromides. As illustrated, the bromination product stream 8 may be first cooled against the bromination feed gas stream 3 in the bromination feed/product cross heat exchanger 88. While not illustrated, the bromination product stream 8 may be further cooled, in some embodiments, by exchanging heat with one or more other process streams in one or more cross heat exchangers. In one embodiment, the bromination product stream 8 may then be cooled, for example, to a temperature of about 33° C. to about 43° C., by exchanging heat with water stream 92 in water-cooled heat exchanger 94. It should be understood that a cooling medium other than water stream 92 may be used in some embodiments, for example, to obtain a lower temperature (e.g., about −10° C. to about 33° C.) for the bromination product stream 8 exiting the heat exchanger 94. The cooled bromination product stream 8, which partially condenses in the water-cooled heat exchanger 94, may then be sent, in one embodiment, to an inlet separator 96 (e.g., drum) for vapor-liquid phase separation. As illustrated, the bromination product stream 8 may be separated into a gas stream 98 and a liquid stream 100 in the inlet separator 96. The liquid stream 100 may be introduced into a lower section of the alkyl bromides fractionator 90 via pump 102. In some embodiments, the alkyl bromides fractionator 90 may include a liquid distributor or manifold (not shown) to more evenly distribute the liquid stream 100 throughout the internal cross sectional area of the alkyl bromides fractionator 90. The alkyl bromides fractionator 90 may comprise a number of trays or equivalent packing material, identified in FIG. 5 by reference number 104. The gas stream 98 from the inlet separator 96 may be further cooled, for example, to a temperature of about 10° C. to about 30° C., by exchanging heat in feed/overheads cross heat exchanger 106 with the gaseous alkane/HBr stream 16 from the overhead of the alkyl bromides fractionator 90 before being introduced into a higher section of the alkyl bromides fractionator 90.

In accordance with present embodiments, the alkyl bromides fractionator 90 should separate $CH_3Br$ and heavier bromides from the effluent gas as a bottoms liquid product. The alkyl bromides fractionator 90 may operate at a pressure of about 1 bar to about 50 bars, alternatively about 20 bars to about 40 bars, and alternatively about 30 bars to about 35 bars. As illustrated, the bottoms liquid product can be withdrawn from at or near the bottom of the alkyl bromides fractionator 90 via liquid alkyl bromides stream 14. Liquid alkyl bromides stream 14 should generally comprise monobrominated alkanes (e.g., $CH_3Br$ and other heavier monobrominated alkanes) and polybrominated alkanes (e.g., $CH_2Br_2$ and other heavier polybrominated alkanes). In some embodiments, the liquid alkyl bromides stream 14 may comprise less than about 2% by weight of the total HBr introduced into the alkyl bromides fractionator 90, alternatively less than about 1%, and alternatively less than about 0.1%. A second bottoms stream 108 comprising $CH_3Br$ and other heavier bromides be withdrawn from at or near the bottom of the alkyl bromides fractionator 90 and vaporized in reboiler 110, for example, by means of steam 112 in a manner that will be evident to those of ordinary skill in the art before being introduced back into the alkyl bromides fractionator 90 at or near the bottom thereof. In some embodiments, the reboiler 110 may operate to heat the second bottoms stream 108 to a temperature of about 100° C. to about 200° C., and about 130° C. to about 170° C., in another embodiment.

An overhead vapor stream 114 may be withdrawn at or near the top of the alkyl bromides fractionator 90 and partially condensed in a reflux condenser 116 against a refrigerant 118 and conveyed to a reflux separator drum 120. The reflux condenser 116 may operate to cool the overhead vapor stream 114 to a temperature of about −40° C. to about 0° C. In some embodiments, the overhead vapor stream 114 is cooled to a temperature warmer than about −40° C. and warmer than −34° C., in another embodiment. The reflux condenser 116 may have an operating pressure, for example, of about 20 bars to about 40 bars. The refrigerant 118 in the reflux condenser 116 may include, for example, propane or other available refrigerants. In the reflux separator drum 120, the overhead vapor stream 114 that was partially condensed in the reflux condenser 116 can be separated into a reflux stream 122 and a gaseous alkane/HBr stream 16. The reflux stream 122 may be conveyed via reflux pump 124 back into the alkyl bromides fractionator 90 at or near the top thereof. As illustrated, the gaseous alkane/HBr stream 16 exiting the reflux separator drum 120 may cross exchange in an overheads cross heat exchanger 126 with the overhead vapor stream 114 entering the reflux condenser 116 and in a feed/overheads cross heat exchanger 106 with the gas stream 98 entering the alkyl bromides fractionator 90, for example, to reduce refrigerant use. The gaseous alkane/HBr stream 16 from the reflux separator drum 120 may comprise, for example, HBr and unreacted alkanes (e.g., primarily methane with some heavier alkanes, such as ethane). In some embodiments, the gaseous alkane/HBr stream 16 comprises less than about 100 mppm alkyl bromides, alternatively less than about 10 mppm alkyl bromides, and alternatively less than about 1 mppm alkyl bromides. In accordance with present embodiments, the gaseous alkane/HBr stream 16 may be routed to other process units (e.g., second HBr separator 56 illustrated on FIG. 1) without entering the synthesis reactor 24.

As illustrated, the liquid alkyl bromides stream 14 from the bottom of the alkyl bromides fractionator 90 may be routed to the polybromides fractionator 128. Prior to entering the polybromides fractionator 128, the liquid alkyl bromides stream 14 may be pumped to a higher pressure or let down to lower pressure, as desired for a particular application. In the illustrated embodiment, the liquid alkyl bromides stream 14 may be let down to a lower pressure across valve 130. The polybromides fractionator 128 may operate, for example, at a pressure of about 1 bar to about 30 bars, and alternatively, about 10 bars to about 20 bars. In some embodiments, the polybromides fractionator 128 may include a liquid distributor or manifold (not shown) to more evenly distribute the liquid alkyl bromides stream 14 throughout the internal cross sectional area of the polybromides fractionator 128. The polybromides fractionator 128 may comprise a number of trays or equivalent packing material, identified in FIG. 5 by reference number 132.

In accordance with present embodiments, the polybromides fractionator 128 should separate the liquid alkyl bromides stream 14 into a monobromides stream 20 comprising $CH_3Br$ and other heavier monobrominated alkanes and a polybromides stream 22 comprising $CH_2Br_2$ and other heavier polybrominated alkanes. As illustrated, the polybromides stream 22 can be withdrawn from at or near the bottom of the polybromides fractionator 128. In some embodiments, the polybromides stream 22 may comprise more than about 0.1 weight % monobrominated alkanes, alternatively, more than about 1 weight % monobrominated alkanes, and alternatively more than about 10 weight % monobrominated alkanes. It should be understood that the content of monobrominated alkanes in polybromides stream 22 can be controlled, in some embodiments, for bottoms temperature control, avoiding potential overheating of the polybromides fractionator 128 bottoms and subsequent polybromides degradation at high temperatures. As previously mentioned, the polybromides stream 22 may be recycled to the bromination reactor 6 via pump 133, as shown on FIG. 5. A second bottoms stream 134 comprising $CH_2Br_2$ and other heavier polybromides can be withdrawn from at or near the bottom of the polybromides fractionator 128 and vaporized in reboiler 136, for example, by means of steam 138 in a manner that will be evident to those of ordinary skill in the art before being introduced back into the polybromides fractionator 128 at or near the bottom thereof. In some embodiments, the reboiler 136 may operate to heat the second bottoms stream 134 to a temperature of about 150° C. to about 250° C., and about 150° C. to about 180° C., in another embodiment. Those of ordinary skill in the art should appreciate, with the benefit of this disclosure, that the temperature of reboiler 136 should be controlled, for example, to minimize the risk of polybromides polymerization and fouling.

The overhead vapor stream 140 may be withdrawn at or near the top of the polybromides fractionator 128 and partially condensed in reflux condenser 142 against a coolant 144 and conveyed to a reflux separator drum 146. The reflux condenser 142 may operate to cool the overhead vapor stream 140 to a temperature warmer than about 37° C., in one embodiment, and warmer than about 43° C. in another embodiment. The coolant 144 in the reflux condenser 142 may include, for example, water, air, or other available cooling medium. In the reflux separator drum 146, the overhead vapor stream 140 that was partially condensed in the reflux condenser 142 can be separated into a reflux stream 148 and a monobromides stream 20. The reflux stream 148 may be conveyed via reflux pump 150 back into the polybromides fractionator 128 at or near the top thereof. The monobromides stream 20 from the reflux separator drum 146 may comprise, for example, $CH_3Br$ and other heavier monobrominated alkanes. In some embodiments, the monobromides stream 20 may comprise less than about 1,000 mppm polybrominated alkanes, alternatively less than about 100 mppm polybrominated alkanes, alternatively less than about 10 mppm polybrominated alkanes, and alternatively less than about 1 mppm polybrominated alkanes. In accordance with some embodiments, the monobromides stream 20 may be routed to the synthesis reactor 24 (e.g., shown on FIG. 1) for production of higher molecular weight hydrocarbons. In some embodiments, the monobromides stream 20 may be recovered as a liquid, for example, when desired to operate the synthesis reactor 24 at a higher pressure than the polybromides fractionator 128.

While the preceding description is directed to bromine-based processes for the conversion of lower molecular weight alkanes to higher molecular weight hydrocarbons, it should be understood that chlorine or another suitable halogen may be used in accordance with present embodiments. Additionally, it should be understood that the present invention also encompasses conversion of lower molecular weight alkanes to other higher molecular weight hydrocarbons. For example, a catalyst may be selected in the synthesis reactor 24 (e.g., shown on FIG. 1) for the production of olefins from alkyl bromides in a manner that will be evident to those of ordinary skill in the art.

To facilitate a better understanding of the present invention, the following examples of certain aspects of some embodiments are given. The following examples should not be read or construed in any manner to limit, or define, the entire scope of the invention.

EXAMPLE 1

Simulations were conducted using Aspen Hysys V7.1 to analyze the inclusion of a polybromides fractionation unit in a process for converting natural gas to liquid hydrocarbons via a bromine-based method. 50 MMSCFD of natural gas was fed to a first process for converting natural gas to liquid hydrocarbons via a bromine-based method. The first process was similar to the process illustrated by FIG. 1, but without a polybromides fractionation unit, e.g., instead of feeding the polybromides fractionation unit, the liquid alkyl bromides stream from the alkyl bromides fractionation unit fed the synthesis reactor. A bromination feed gas stream comprising a Cl/Br$_2$ mixture having a Cl/Br$_2$ molar ratio of 2.5 was fed to the bromination reactor at a temperature of 200° C. to 400° C. and 35 barg and left at a temperature of 450° C. to about 500° C. In the bromination reactor, essentially all of the Br$_2$ was consumed, resulting in a bromination product stream comprised of 3,378 kmol/h HBr, 5,950 kmol/h unreacted Cl, and 2,494 kmol/h Cl bromide products. The bromide selectivity profile was: 70 mol % CH$_3$Br, 25 mol % CH$_2$Br$_2$, and 5 mol % other bromides and solid carbonaceous compounds. Distilling the bromination product stream in an alkyl bromides fractionator produced a 9,293 kmol/h alkane/HBr stream as an overhead stream and a 2,528 kmol/h liquid alkyl bromides stream as a bottom stream. The liquid alkyl bromides stream containing 24 mol % CH$_2$Br$_2$ was fed to the synthesis reactor generating higher molecular weight hydrocarbons and HBr. The resultant synthesis product stream was then routed to an HBr separator to recover 3,411 kmol/h HBr into a recirculating aqueous solution. The alkane/HBr stream from the overhead of the alkyl bromides fractionator was routed to a second HBr separator to generate 5,950 kmol/h Cl recyclable to the bromination reactor after dehydration and to recover 3,343 kmol/h HBr into a second recirculating aqueous solution. The first and second recirculating aqueous solutions containing HBr dissolved therein produced from the HBr separators were combined and routed to a bromination oxidation unit to convert the dissolved bromide to 3,378 kmol/h elemental bromine for reuse in the bromination reactor.

50 MMSCFD of natural gas was fed to a second process for converting natural gas to liquid hydrocarbons via a bromine-based method. The second process is illustrated by FIG. 1 and comprises an alkyl bromides fractionation unit to separate out Cl/HBr from Cl bromides and a polybromides fractionation unit to separate out CH$_2$Br$_2$ and heavier polybromides from Cl bromides prior to feeding it to the synthesis reactor. A bromination feed gas stream comprising a Cl/Br$_2$ mixture having a Cl/Br$_2$ molar ratio of 2.5 along with a 1,798 kmol/h recycle polybromides stream was fed to the bromination reactor at a temperature of 200° C. to 400° C. and 35 Barg and left at a temperature of 450° C. to 500° C. In the bromination reactor, essentially all of the Br$_2$ was consumed, resulting in a bromination product stream comprised of 2,564 kmol/h HBr, 3,804 kmol/h unreacted Cl, and 4,292 kmol/h Cl bromide products. The bromide selectivity profile was: 68 mol % CH$_3$Br, 29 mol % CH$_2$Br$_2$, and 3 mol % other bromides and solid carbonaceous compounds. Distilling the bromination product stream in a first fractionator (alkyl bromides fractionator) and then the first column bottom stream (liquid alkyl bromides stream) in a second fractionator (polybromides fractionator), produced a 6,343 kmol/h alkane/HBr stream, a 2,498 kmol/h monobromides stream, and a 1,798 kmol/h polybromides stream. The monobromides stream containing 0.1 mol % CH$_2$Br$_2$ was fed to the synthesis reactor in generating higher molecular weight hydrocarbons and HBr. The resultant synthesis product stream was then routed to an HBr separator to recover 2,500 kmol/h HBr into a recirculating aqueous solution. The alkane/HBr stream from the overhead of the alkyl bromides fractionator was routed to a second HBr separator to generate 3,804 kmol/h Cl recyclable to the bromination reactor after dehydration and to recover a 2,538 kmol/h HBr into a second recirculating aqueous solution. The first and second recirculating aqueous solutions containing HBr dissolved therein produced from the two HBr separators were combined and routed to a bromination oxidation unit to convert the dissolved bromide to a 2,519 kmol/h elemental bromine for reuse in the bromination reactor.

The above results are summarized in Table 1. It shows that using the second process with the polybromides fractionation unit, as illustrated in FIG. 1, the utilization efficiency of Br$_2$ significantly increased, requiring 25.4% less Br$_2$ (reduced from 3,378 to 2,519 kmol/h) to process the same amount of natural gas feed while using the same Cl/Br$_2$ molar ratio in the bromination reactor. The concentration of CH$_2$Br$_2$ in the feed to the synthesis reactor was also significantly reduced from 24 to 0.1 mol %.

TABLE 1

|  |  | First process (without Polybromides Fractionation) | Second process (with Polybromides Fractionation) |
|---|---|---|---|
| Natural Gas feed capacity | (MMSCFD) | 50 | 50 |
| Cl/Br2 molar ratio in bromination reactor |  | 2.5:1 | 2.5:1 |
| Br$_2$ circulation rate | (kgmol/h) | 3,378 | 2,519 |
| CH$_2$Br$_2$ content in the feed to coupling reactor | (mol %) | 24 | 0.1 |

EXAMPLE 2

Additional simulations were conducted using Aspen Hysys V7.1 to further analyze the inclusion of a polybromides fractionation unit in a process for converting natural gas to liquid hydrocarbons via a bromine-based method. 50 MMSCFD of natural gas was fed to a process for converting natural gas to liquid hydrocarbons via a bromine-based method. A bromination feed gas stream comprising a Cl/$Br_2$ mixture having a $C_1$/$Br_2$ molar ratio of 2.5 along with a recycle polybromides stream entered the bromination reactor at a temperature of 200° C. to 400° C. and 35 Barg and left at a temperature of 450° C. to 500° C. Excluding carbonaceous solid compounds, the bromination product stream comprised of 24 mol % HBr, 36 mol % Cl, and 40 mol % Cl bromides fed a first distillation column (alkyl bromides fractionator) at a rate of 10,639 kgmol/h. Referring to FIG. 5, this column fractionated the bromination product stream into a 6,343 kgmol/h alkane/HBr stream as an overhead product at 32 barg containing essentially all of the HBr and Cl and a 4,296 kgmol/h liquid alkyl bromides stream as a bottom product containing $CH_3Br$ and heavier bromides. The column specifications included 1% HBr recovery in the bottom and 1 mppm $CH_3Br$ in the overheads. The condenser temperature was −4.4° C. requiring a refrigeration duty of 10 MW. The reboiler temperature was 171° C. requiring a steam duty of 27 MW.

The liquid alkyl bromides stream from the bottom of the alkyl bromides fractionator was then let down to 15 barg and fed to a second distillation column (polybromides fractionator). The second column fractionated the feed into an a 2,498 kgmol/h monobromides stream as an overhead product containing essentially pure $CH_3Br$ and a 1,798 kmol/h polybromides stream as a bottom product enriched in $CH_2Br_2$ and heavier bromides. The column specifications included 0.1 mol % $CH_2Br_2$ in the overhead and the reboiler temperature of 171° C. The condenser temperature was 102° C. requiring a cooling duty of 5 MW. The reboiler required a steam duty of 13 MW.

The above results are summarized in Table 2.

TABLE 2

|  |  | Alkyl Bromides Fractionator | Polybromides Fractionator |
|---|---|---|---|
| Feed rate | (kgmol/h) | 10,639 | 4,296 |
| Overhead rate | (kgmol/h) | 6,343 | 2,498 |
| Bottoms rate | (kgmol/h) | 4,296 | 1,798 |
| Condenser temperature | (° C.) | −4.4 | 102 |
| Condenser duty | (MW) | 10 | 5 |
| Reboiler temperature | (° C.) | 171 | 171 |
| Reboiler duty | (MW) | 27 | 13 |

Certain embodiments of the methods of the invention are described herein. Although major aspects of what is to believed to be the primary chemical reactions involved in the methods are discussed in detail as it is believed that they occur, it should be understood that side reactions may take place. One should not assume that the failure to discuss any particular side reaction herein means that that reaction does not occur. Conversely, those that are discussed should not be considered exhaustive or limiting. Additionally, although figures are provided that schematically show certain aspects of the methods of the present invention, these figures should not be viewed as limiting on any particular method of the invention.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. All numbers and ranges disclosed above may vary by some amount. Whenever a numerical range with a lower limit and an upper limit is disclosed, any number and any included range falling within the range are specifically disclosed.

What is claimed is:

1. A process comprising:
   reacting at least gaseous alkanes and a halogen to produce at least a halogenation product stream, wherein the halogenation product stream comprises alkyl halides, hydrogen halide, and unreacted alkanes;
   separating the halogenation product stream into at least a gaseous stream and a liquid alkyl halides stream, wherein the gaseous stream comprises hydrogen halide and unreacted alkanes, and wherein the liquid alkyl halides stream comprises alkyl halides;
   separating the liquid alkyl halides stream into at least a monohalides stream and a polyhalides stream, wherein the monohalides stream comprises monohalogenated alkanes, and wherein the polyhalides stream comprises polyhalogenated alkanes; and
   reacting at least a portion of the monohalogenated alkanes from the monohalides stream in the presence of a catalyst to produce at least a synthesis product stream, wherein the synthesis product stream comprises higher molecular weight hydrocarbons and hydrogen halide.

2. The process of claim 1 wherein the halogen comprises bromine.

3. The process of claim 1 wherein the gaseous alkanes comprise alkanes having 2 or more carbons in an amount of less than about 0.1 mole % to less than about 10 mole %.

4. The process of claim 1 wherein the step of separating the halogenation product stream comprises:
   cooling the halogenation product stream;
   separating the halogenation product stream into a liquid fractionator feed stream and a gaseous fractionator feed stream; and
   feeding the liquid fractionator feed stream and the gaseous fractionator feed stream into a fractionator, wherein the gaseous stream and the liquid alkyl halides stream are withdrawn from the fractionator.

5. The process of claim 4 wherein the fractionator operates at a pressure of about 20 bars to about 40 bars.

6. The process of claim 4 further comprising:
   withdrawing a second liquid stream from the fractionator and heating the second liquid stream to a temperature of about 100° C. to about 200° C. in a reboiler; and
   withdrawing an overhead vapor stream from the fractionator and cooling the overhead vapor stream to a temperature warmer than about −40° C. in a condenser.

7. The process of claim 6 further comprising cooling the overhead vapor stream against the gaseous stream.

8. The process of claim 4 further comprising:
cooling the gaseous fractionator feed stream against the gaseous stream; and
cooling the halogenation product stream against a halogenation feed stream comprising the gaseous alkanes and the halogen from the step of reacting at least gaseous alkanes and a halogen.

9. The process of claim 1 wherein the liquid alkyl halides stream comprises less than about 2% by weight of the hydrogen halide from the halogenation product stream.

10. The process of claim 1 wherein the unreacted alkanes in the gaseous stream comprises methane and alkanes having 2 or more carbons in an amount of less than about 1% by mole.

11. The process of claim 1 wherein the gaseous stream comprises less than about 10 mppm alkyl halides.

12. The process of claim 1 further comprising reducing the liquid alkyl halides stream to a pressure of about 1 bar to about 30 bars.

13. The process of claim 1 wherein the step of separating the liquid alkyl halides stream into at least a monohalides stream and a polyhalides stream comprises: feeding the liquid alkyl halides stream into a second fractionator, wherein the monohalides stream and the polyhalides stream are withdrawn from the second fractionator.

14. The process of claim 13 further comprising:
withdrawing a liquid stream from the second fractionator and heating the liquid stream to a temperature of about 150° C. to about 250° C. in a reboiler; and
withdrawing an overhead vapor stream from the second fractionator and cooling the overhead vapor stream to a temperature warmer than about 37° C. in a condenser.

15. The process of claim 12 wherein the monohalides stream comprises monohalogenated methane, wherein polyhalogenated alkanes are present in the monohalides stream in an amount less than about 100 mppm.

16. The process of claim 1 further comprising:
recovering at least a portion of the hydrogen halide from the gaseous stream; and
recovering at least a portion of the hydrogen halide from the synthesis product stream, wherein recovery of the hydrogen halide from the synthesis product stream occurs in the same unit as the recovery of the hydrogen halide from the gaseous stream.

17. The process of claim 1 further comprising:
recovering at least a portion of the hydrogen halide from the gaseous stream; and
recovering at least a portion of the hydrogen halide from the synthesis product stream; wherein recovery of the hydrogen halide from the synthesis product stream occurs in a different unit than the recovery of the hydrogen halide from the gaseous stream.

18. The process of claim 1 further comprising reacting the gaseous alkanes with at least a portion of the polyhalogenated alkanes from the polyhalides stream to convert at least a portion of the polyhalogenated alkanes to monohalogenated alkanes.

19. The process of claim 1 further comprising reacting at least a portion of the polyhalogenated alkanes from the polyhalides stream with light end hydrocarbons to convert at least a portion of the alkyl halides from polyhalogenated alkanes to monohalogenated alkanes.

20. The process of claim 1 further comprising separating light end hydrocarbons from at least the higher molecular weight hydrocarbons and a natural gas feed, the light end hydrocarbons having from 2 carbons to 4 carbons.

21. The process of claim 20 further comprise reacting at least a portion of the light-end hydrocarbons with a halogen to form a stream comprising alkyl halides and hydrogen halide; and reacting at least a portion alkyl halides in the presence of the catalyst.

22. The process of claim 1 wherein the catalyst comprises a synthetic crystalline alumino-silicate catalyst.

23. A process comprising
reacting at least gaseous alkanes and bromine in a bromination reactor to produce at least a bromination product stream, wherein the bromination product stream comprise alkyl bromides, hydrogen bromide, and unreacted alkanes;
separating the bromination product stream into at least a gaseous alkane/HBr stream and a liquid alkyl bromides stream, wherein the gaseous alkane/HBr stream comprises hydrogen bromide and unreacted alkanes, and wherein the liquid alkyl bromides stream comprises alkyl bromides;
separating the liquid alkyl bromides stream into at least a monobromides stream and a polybromides stream, wherein the monobromides stream comprises monobrominated alkanes, and wherein the polybromides stream comprises polybrominated alkanes;
reacting at least a portion of the monobrominated alkanes from the monobromides stream in a synthesis reactor to produce at least a synthesis product stream, wherein the synthesis product stream comprises higher molecular weight hydrocarbons and hydrogen bromide;
recovering at least a portion of the hydrogen bromide from the synthesis product stream in a hydrogen bromide separator;
providing a natural gas stream;
separating at least the synthesis product stream and the natural gas stream into at least a light ends product stream, a heavy ends product stream, and a feed gas stream, wherein the light ends product stream comprises light end hydrocarbons having from 2 carbons to 4 carbons, wherein the heavy ends product stream comprises heavy end hydrocarbons having 5 or more carbons, and wherein the feed gas stream comprises methane;
compressing the feed gas stream in a feed compressor;
feeding the feed gas stream into the bromination reactor;
generating a recycle alkane stream by recovering at least a portion of the hydrogen bromide from the gaseous alkane/HBr stream in a second hydrogen bromide separator operating at a higher pressure than the hydrogen bromide separator;
compressing the recycle alkane stream in a recycle compressor; and
feeding the recycle alkane stream to the bromination reactor.

24. The process of claim 23 wherein the step of separating the bromination product stream comprises:
cooling the bromination product stream;
separating the bromination product stream into a liquid fractionator feed stream and a gaseous fractionator feed stream; and
feeding the liquid fractionator feed stream and the gaseous fractionator feed stream into an alkyl bromides fractionator, wherein the gaseous alkane/HBr stream and the liquid alkyl bromides stream are withdrawn from the alkyl bromides fractionator, and wherein the alkyl bromides fractionator operates at a pressure of about 20 bars to about 40 bars.

25. The process of claim 23 wherein the liquid alkyl bromides stream comprises less than about 2% by weight of the hydrogen bromide from the bromination product stream.

26. The process of claim 23 wherein the gaseous alkane/HBr stream comprises less than about 10 mppm alkyl bromides.

27. The process of claim 23 further comprising feeding the polybromides stream to the bromination reactor such that at least a portion of the polybrominated alkanes react with the gaseous alkanes to convert at least a portion of the polybrominated alkanes to monobrominated alkanes.

28. The process of claim 23 further comprising reacting at least a portion of the polybrominated alkanes from the polybromides stream with at least a portion of the light end hydrocarbons from the light-ends product stream to convert at least a portion of the polybrominated alkanes to monobrominated alkanes.

29. The process of claim 23 further comprising:
reacting bromine and at least a portion of the light end hydrocarbons from the light-end hydrocarbon stream to form a brominated stream comprising brominated light end hydrocarbons, hydrogen bromide, and unreacted light end hydrocarbons; and
reacting at least a portion of the brominated light end hydrocarbons in the presence of the catalyst in the synthesis reactor.

30. The process of claim 23 wherein the catalyst comprises a synthetic crystalline alumino-silicate catalyst.

* * * * *